US012233241B2

(12) United States Patent
Rinehart et al.

(10) Patent No.: US 12,233,241 B2
(45) Date of Patent: Feb. 25, 2025

(54) METHODS AND SYSTEMS TO VALIDATE PHYSIOLOGIC WAVEFORM RELIABILITY AND USES THEREOF

(71) Applicant: The Regents of the University of California, Oakland, CA (US)

(72) Inventors: Joseph B. Rinehart, Newport Beach, CA (US); Michael Ma, Santa Ana, CA (US)

(73) Assignee: The Regents of the University of California, Oakland, CA (US)

( * ) Notice: Subject to any disclaimer, the term of this patent is extended or adjusted under 35 U.S.C. 154(b) by 926 days.

(21) Appl. No.: 17/170,492

(22) Filed: Feb. 8, 2021

(65) Prior Publication Data
US 2021/0244882 A1 Aug. 12, 2021

Related U.S. Application Data

(60) Provisional application No. 63/025,761, filed on May 15, 2020, provisional application No. 62/971,594, filed on Feb. 7, 2020.

(51) Int. Cl.
*A61M 5/172* (2006.01)
*A61B 5/00* (2006.01)
(Continued)

(52) U.S. Cl.
CPC ......... *A61M 5/1723* (2013.01); *A61B 5/4839* (2013.01); *A61B 5/7221* (2013.01);
(Continued)

(58) Field of Classification Search
None
See application file for complete search history.

(56) References Cited

U.S. PATENT DOCUMENTS 4,080,966 A 3/1978 Mcnally et al.
4,280,494 A 7/1981 Cosgrove, Jr. et al.
(Continued)

FOREIGN PATENT DOCUMENTS

CN 115279262 A 11/2022
EP 4099899 A1 12/2022
(Continued)

OTHER PUBLICATIONS

International Search Report and Written Opinion for International Application No. PCT/US2021/017101, Search completed Apr. 8, 2021, Mailed Apr. 26, 2021, 19 pgs.
(Continued)

*Primary Examiner* — Jenna Zhang
(74) *Attorney, Agent, or Firm* — KPPB LLP

(57) ABSTRACT

Methods and systems to validated physiologic waveform reliability and uses thereof are provided. A number of embodiments describe methods to validate waveform reliability, including blood pressure waveforms, electrocardiographic waveforms, and/or any other physiological measurement producing a continuous waveform. Certain embodiments output reliability measurements to closed loop systems that can control infusion rates of cardioactive drugs or other fluids in order to regulate blood pressure, cardiac rate, cardiac contractility, and/or vasomotor tone. Further embodiments allow for waveform evaluators to validate waveform reliability based on at least one waveform feature using data collected from clinical monitors using machine learning algorithms.

24 Claims, 16 Drawing Sheets

(51) Int. Cl.
| | |
|---|---|
| A61K 31/137 | (2006.01) |
| G06N 5/04 | (2023.01) |
| G06N 20/00 | (2019.01) |
| G16H 20/17 | (2018.01) |
| G16H 50/30 | (2018.01) |

(52) U.S. Cl.
CPC .......... *A61B 5/7267* (2013.01); *A61K 31/137* (2013.01); *G06N 5/04* (2013.01); *G06N 20/00* (2019.01); *G16H 20/17* (2018.01); *G16H 50/30* (2018.01); *A61M 2230/04* (2013.01); *A61M 2230/30* (2013.01); *A61M 2230/65* (2013.01)

(56) References Cited

U.S. PATENT DOCUMENTS

| | | | |
|---|---|---|---|
| 4,425,920 | A | 1/1984 | Bourland et al. |
| 4,457,751 | A | 7/1984 | Rodler |
| 4,688,577 | A | 8/1987 | Bro |
| 5,733,259 | A | 3/1998 | Valcke et al. |
| 5,895,359 | A | 4/1999 | Peel, III |
| 9,307,913 | B2 | 4/2016 | O'Brien et al. |
| 9,867,936 | B2 | 1/2018 | Sia |
| 10,137,245 | B2 | 11/2018 | Melker et al. |
| 2002/0095090 | A1* | 7/2002 | Caro ............... A61B 5/022 600/485 |
| 2004/0167408 | A1 | 8/2004 | Ashida et al. |
| 2009/0131805 | A1* | 5/2009 | O'Brien ............ A61B 5/02028 600/485 |
| 2010/0228102 | A1 | 9/2010 | Addison et al. |
| 2011/0112379 | A1 | 5/2011 | Li et al. |
| 2013/0226138 | A1* | 8/2013 | Sia ................. A61M 5/16827 604/66 |
| 2013/0276785 | A1* | 10/2013 | Melker ............ A61M 16/0677 128/204.23 |
| 2014/0031652 | A1 | 1/2014 | Baker, Jr. |
| 2018/0085012 | A1* | 3/2018 | Wei .................. A61B 5/0245 |
| 2019/0231196 | A1 | 8/2019 | Kim |
| 2020/0196878 | A1* | 6/2020 | Bentzion ............ A61B 5/1118 |

FOREIGN PATENT DOCUMENTS

| | | | | |
|---|---|---|---|---|
| JP | 2023514150 | A | 4/2023 | |
| WO | WO-2018210985 | A1 * | 11/2018 | ........ A61B 5/02108 |
| WO | 2021159083 | A1 | 8/2021 | |

OTHER PUBLICATIONS

Abbott et al., "A Prospective International Multicentre Cohort Study of Intraoperative Heart Rate and Systolic Blood Pressure and Myocardial Injury After Noncardiac Surgery: Results of the Vision Study", Anesthesia & Analgesia, Jun. 2018, vol. 126, Issue 6, pp. 1936-1945, doi: 10.1213/ANE.0000000000002560.

Bijker et al., "Intraoperative hypotension and perioperative ischemic stroke after general surgery: a nested case-control study", Anesthesiology, Mar. 2012, vol. 116, No. 3, pp. 658-664, doi: 10.1097/ALN.0b013e3182472320.

Cannesson, "Arterial pressure variation and goal-directed fluid therapy", Journal of Cardiothoracic and Vascular Anesthesia, Jun. 1, 2010, vol. 24, Issue 3, pp. 487-497, DOI:https://doi.org/10.1053/j.jvca.2009.10.008.

Cannesson et al., "Machine learning of physiological waveforms and electronic health record data to predict, diagnose and treat haemodynamic instability in surgical patients: protocol for a retrospective study", BMJ Open, 2019. vol. 9, e031988, pp. 1-7, doi: 10.1136/bmjopen-2019-031988.

Cunningham et al., "Changes in mean blood pressure caused by damping of the arterial pressure waveform", Early Human Development, Jan. 1994, vol. 36, No. 1, pp. 27-30, doi: 10.1016/0378-3782(94)90030-2.

De Hert et al., "Evaluation of left ventricular function in anesthetized patients using femoral artery dP/dt(max)", Journal of Cardiothoracic and Vascular Anesthesia, Jun. 2006, vol. 20, No. 3, pp. 325-330, published online Feb. 20, 2006, doi: 10.1053/j.jvca.2005.11.006.

Esper et al., "Arterial waveform analysis", Best Practice & Research Clinical Anaesthesiology, Dec. 2014, vol. 28, Issue 4, pp. 363-380, https://doi.org/10.1016/j.bpa.2014.08.002.

Gu et al., "Association between intraoperative hypotension and 30-day mortality, major adverse cardiac events, and acute kidney injury after non-cardiac surgery: A meta-analysis of cohort studies", International Journal of Cardiology, May 1, 2018, vol. 1, No. 258, pp. 68-73, Epublished Feb. 2, 2018, doi: 10.1016/j.ijcard.2018.01.137.

Hallqvist et al., "Intraoperative hypotension is associated with acute kidney injury in noncardiac surgery", European Society of Anaesthesiology, 2018, vol. 35, pp. 273-279, published online Nov. 27, 2017, DOI:10.1097/EJA.0000000000000735.

Hallqvist et al., "Intraoperative hypotension is associated with myocardial damage in noncardiac surgery", European Journal of Anaesthesiology, Jun. 2016, vol. 33. Issue 6, pp. 450-456, doi: 10.1097/EJA.0000000000000429.

Hatib et al., "Machine-learning Algorithm to Predict Hypotension Based on High-fidelity Arterial Pressure Waveform Analysis", Anesthesiology, Oct. 2018, vol. 129, pp. 663-674, https://doi.org/10.1097/ALN.0000000000002300.

Jooesten et al., "Feasibility of closed-loop titration of norepinephrine infusion in patients undergoing moderate- and high-risk surgery", British Journal of Anaesthesia, 2019, vol. 123, No. 4, pp. 430-438, Advance Access publication date Jun. 27, 2019. doi: 10.1016/j.bja.2019.04.064.

Joosten et al., "Automated Titration of Vasopressor Infusion Using a Closed-loop Controller: In Vivo Feasibility Study Using a Swine Model", Anesthesiology, vol. 130, No. 3, Mar. 2019, pp. 394-403.

Kee et al., "Closed-Loop Feedback Computer-Controlled Phenylephrine for Maintenance of Blood Pressure During Spinal Anesthesia for Cesarean Delivery: A Randomized Trial Comparing Automated Boluses Versus Infusion", Anesthesia & Analgesia, Jul. 2017. vol. 125, Issue 1, pp. 117-123, doi: 10.1213/ANE.0000000000001974.

Kirchhof et al., "Mean arterial pressure readings: variations with positions and transducer level", Nursing Research, Nov.-Dec. 1984, vol. 33, No. 6, pp. 343-345.

Maheshwari et al., "Prolonged concurrent hypotension and low bispectral index ('double low') are associated with mortality, serious complications, and prolonged hospitalization after cardiac surgery", British Journal of Anaesthesia, 2017, vol. 119, No. 1, pp. 40-49, doi: 10.1093/bja/aex095.

Maheshwari et al., "The association of hypotension during non-cardiac surgery, before and after skin incision, with postoperative acute kidney injury: a retrospective cohort analysis", Anaesthesia, 2018, vol. 73, pp. 1223-1228, doi:10.1111/anae.14416.

Maheshwari et al., "The relationship between ICU hypotension and in-hospital mortality and morbidity in septic patients", Intensive Care Medicine, Jun. 5, 2018, vol. 44, pp. 857-867, https://doi.org/10.1007/s00134-018-5218-5.

Marques et al., "Physician-Directed Versus Computerized Closed-Loop Control of Blood Pressure Using Phenylephrine in a Swine Model", Anesthesia & Analgesia, Jul. 2017, vol. 125, No. 1, pp. 110-116. doi: 10.1213/ANE.0000000000001961.

Nguyen et al., "Hypotension and a positive fluid balance are associated with delirium in patients with shock", PLoS One, Aug. 7, 2018, vol. 13, No. 8, e0200495, 16 pgs., doi: 10.1371/journal.pone.0200495.

Pedregosa et al., "Scikit-learn: Machine Learning in Python", Journal of Machine Learning Research, Oct. 2011, vol. 12, pp. 2825-2830.

Rinehart et al., "Blood pressure variability in surgical and intensive care patients: Is there a potential for closed-loop vasopressor administration?", Anaesthesia Critical Care & Pain Medicine, Feb. 2019, vol. 38, Issue 1, pp. 69-71, https://doi.org/10.1016/j.accpm.2018.11.009.

Rinehart et al., "Closed-loop assisted versus manual goal-directed fluid therapy during high-risk abdominal surgery: a case-control

(56) References Cited

OTHER PUBLICATIONS study with propensity matching", Critical Care, 2015, vol. 19, No. 1, 94, 11 pgs., published online Mar. 19, 2015, doi: 10.1186/s13054-015-0827-7.

Rinehart et al., "Closed-loop vasopressor control: in-silico study of robustness against pharmacodynamic variability", Journal of Clinical Monitoring and Computing, vol. 33, No. 5, Oct. 2019, 8 pgs.

Rinehart et al., "Feasibility of automated titration of vasopressor infusions using a novel closed-loop controller", Journal of Clinical Monitoring and Computing, vol. 32, Jan. 25, 2017, 7 pgs.

Saito et al., "The Precision-Recall Plot is More Informative than the ROC Plot When Evaluating Binary Classifiers on Imbalanced Datasets", PLoS One, Mar. 4, 2015, vol. 10, No. 3, e0118432, 21 pgs., doi: 10.1371/journal.pone.0118432.

Sessler et al., "Period-dependent Associations between Hypotension during and for Four Days after Noncardiac Surgery and a Composite of Myocardial Infarction and Death: A Substudy of the POISE-2 Trial", Anesthesiology, Feb. 2018, vol. 128, No. 2, pp. 317-327, doi: 10.1097/ALN.0000000000001985.

Sessler et al., "Perioperative myocardial injury and the contribution of hypotension", Intensive Care Medicine, Jun. 2018, vol. 44, No. 6, pp. 811-822, published online Jun. 4, 2018, doi: 10.1007/s00134-018-5224-7.

Sessler et al., "Perioperative Quality Initiative consensus statement on intraoperative blood pressure, risk and outcomes for elective surgery", British Journal of Anaesthesia, May 2019, vol. 122, Issue 5, pp. 563-574, Advance Access publication Feb. 27, 2019, doi: https://doi.org/10.1016/j.bja.2019.01.013.

Sharman et al., "Radial pressure waveform dP/dt max is a poor indicator of left ventricular systolic function", European Journal of Clinical Investigation, Apr. 2007, vol. 37, No. 4, pp. 276-281, doi: 10.1111/j.1365-2362.2007.01784.x.

Slagt et al., "Systematic review of uncalibrated arterial pressure waveform analysis to determine cardiac output and stroke volume variation", British Journal of Anaesthesia, Apr. 2014, vol. 112, No. 4, pp. 626-637, published online Jan. 14, 2014, doi: 10.1093/bja/aet429.

Soltesz et al., "Closed-loop regulation of arterial pressure after acute brain death", Journal of Clinical Monitoring and Computing, 2018, vol. 32, No. 3, pp. 429-437, https://doi.org/10.1007/s10877-017-0033-z.

Sun et al., "Association of intraoperative hypotension with acute kidney injury after elective noncardiac surgery", Anesthesiology, Sep. 2015, vol. 123, No. 3, pp. 515-523.

Tartiere et al., "Non-invasive radial pulse wave assessment for the evaluation of left ventricular systolic performance in heart failure", European Journal of Heart Failure, 2007, vol. 9, pp. 477-483, available online Jan. 23, 2007, doi: 10.1016/j.ejheart.2006.11.005.

Tartiere et al., "Noninvasively determined radial dP/dt is a predictor of mortality in patients with heart failure", American Heart Journal, Apr. 2008, vol. 155, Issue 4, pp. 758-763, https://doi.org/10.1016/j.ahj.2007.11.030.

Thiele et al., "Arterial Waveform Analysis for the Anesthesiologist Past, Present, and Future Concepts", Anesthesia & Analgesia: Oct. 2011, vol. 113, Issue 4, pp. 766-776, doi: 10.1213/ANE.0b013e31822773ec.

Varvel et al., "Measuring the predictive performance of computer-controlled infusion pumps", Journal of Pharmacokinetics and Biopharmaceutics, Feb. 1, 1992, vol. 20, pp. 63-94, https://doi.org/10.1007/BF01143186.

Vincent et al., "Mean arterial pressure and mortality in patients with distributive shock: a retrospective analysis of the MIMIC-III database", Annals of Intensive Care, 2018, vol. 8, No. 107, 10 pgs., https://doi.org/10.1186/s13613-018-0448-9.

Wallace et al., "Hemodynamic determinants of the maximal rate of rise of left ventricular pressure", Am J Physiol., Jul. 1963, vol. 205, pp. 30-36, doi: 10.1152/ajplegacy.1963.205.1.30.

Walsh et al., "Relationship between Intraoperative Mean Arterial Pressure and Clinical Outcomes after Noncardiac Surgery: Toward an Empirical Definition of Hypotension", Anesthesiology Sep. 2013, vol. 119, pp. 507-515, https://doi.org/10.1097/ALN.0b013e3182a10e26.

Wesselink et al., "Intraoperative hypotension and the risk of postoperative adverse outcomes: a systematic review", British Journal of Anaesthesia, 2018, vol. 121, No. 4, 706-721, Advance Access publication Jun. 20, 2018, doi: 10.1016/j.bja.2018.04.036.

International Preliminary Report on Patentability for International Application PCT/US2021/017101, Report issued Jul. 28, 2022, Mailed Aug. 18, 2022, 8 Pgs.

Dale et al., "Nasal administration of opioids for pain management in adults", Acta. Anaesthesiol Scand, 2002, vol. 46, pp. 759-770.

Velhorse-Jansse et al., "A review of the clinical pharmacokinetics of opioids, benzodiazepines, and antimigraine drugs delivered intranasally", Clinical Therapeutics, 2009, vol. 31, No. 12, pp. 2954-2987.

Extended European Search Report for European Application No. 21751119.5, Search completed Jan. 29, 2024, Mailed May 7, 2024, 11 Pgs.

Supplementary Partial European Search Report for European Application No. 21751119.5, Search completed Jan. 29, 2024, Mailed Feb. 14, 2024, 15 Pgs.

Hravnak et al., "Real Alerts and Artifact Classification in Archived Multi-Signal Vital Sign Monitoring Data: Implications for Mining Big Data", Journal of Clinical Monitoring and Computing, Springer Netherlands, Dordrecht, Oct. 5, 2015, vol. 30, No. 6, pp. 875-888, XP036085182, ISSN: 1387-1307, DOI: 10.1007/S10877-015-9788-2 [retrieved on Oct. 5, 2015], p. 877-p. 886.

\* cited by examiner

METHODS AND SYSTEMS TO VALIDATE PHYSIOLOGIC WAVEFORM RELIABILITY AND USES THEREOF

CROSS REFERENCE TO RELATED APPLICATIONS

This application claims priority to U.S. Provisional Application Ser. No. 63/025,761, entitled "Methods and Systems to Validate Physiologic Waveform Reliability and Uses Thereof" to Rinehart et al., filed May 15, 2020 and U.S. Provisional Application Ser. No. 62/971,594, entitled "Methods and Systems to Validate Physiologic Waveform Reliability and Uses Thereof" to Rinehart et al., filed Feb. 7, 2020; the disclosures of which are incorporated herein by reference in their entireties.

FIELD OF THE INVENTION

The present invention is directed to systems and methods to assess waveform reliability in blood pressure monitoring, and more particularly to closed-loop controllers, including controllers designed to correct hypotension and/or hypertension.

BACKGROUND OF THE INVENTION

Transient episodes of intraoperative hypotension are associated with adverse cardiovascular, renal, and neurological complications, including organ damage, ischemia, stroke, heart attack, or death. (See e.g., Sessler D I, et al. Anesthesiology 2018; 128: 317-27; Sessler D I and Khanna A K. Intensive Care Med 2018; 44: 811-22; Hallqvist L, et al. Eur J Anaesthesiol 2016; 33: 450-56; Sessler D I, et al. Br J Anaesth 2019 May; 122: 563-74; Maheshwari A, et al. Br J Anaesth 2017 Jul. 1; 119: 40-49; Wesselink E M, et al. Br J Anaesth 2018 October; 121: 706-21; Sun L Y, et al. Anesthesiology 2015; 123: 515-23; Maheshwari K, Anaesthesia 2018; 73: 1223-28; Walsh M, et al. Anesthesiology 2013; 119: 507-15; Gu W J, et al. Int J Cardiol 2018; 258: 68-73; Hallqvist L, et al. Eur J Anaesthesiol 2018; 35: 273-79; and Bijker J B, et al. Anesthesiology 2012; 116: 658-64; the disclosures of which are herein incorporated by reference in their entireties.) Rapid correction of hypotension is, therefore, a key consideration for anaesthesiologists responsible for high-risk surgical and critically ill patients. (See e.g., Vincent J L, et al. Ann Intensive Care 2018; 8: 107; Maheshwari K, et al. Intensive Care Med 2018; 44: 857-67; and Nguyen D N, et al. PLoS One 2018; 13, e0200495; the disclosures of which are herein incorporated by reference in their entireties.)

Vasopressors are frequently used to correct hypotension, especially when patients are unresponsive to other interventions including fluid administration. Vasopressor therapy often requires frequent boluses, adjustment of infusion rates, or both in haemodynamically complex patients. Ideally, such changes should be made expediently to avoid periods of hypotension or hypertension, as both can be deleterious. (See e.g., Abbott T E F, et al. Anesth Analg 2019; 126(6): 1936-45; the disclosure of which is herein incorporated by reference in its entirety.) In current technology, vasopressor infusions are either titrated or administered in boluses by hand. The former is slow in adjusting to changing clinical conditions and the latter results in inaccurate and inconsistent blood pressure management.

SUMMARY OF THE INVENTION

Methods and systems for assessing waveform validity are disclosed.

In one embodiment, a method for validating waveform reliability includes obtaining a blood pressure measurement as a continuous waveform, validating a reliability of the continuous waveform, and outputting a reliability measure of the validated waveform reliability.

In a further embodiment, the validating step uses a machine learning algorithm to evaluate at least one feature of the continuous waveform, variance in the at least one feature, change in the at least one feature, and change in variance of the at least one feature.

In another embodiment, the at least one feature is from a category selected from the group consisting of: pressure, pressure ratio, time, time ration, area, slope, and morphology.

In a still further embodiment, the reliability measure is a qualitative measure of reliable or not reliable.

In still another embodiment, the reliability measure is a quantitative measure of 0-100% confidence.

In a yet further embodiment, the reliability measure is a semi-quantitative measure of not reliable, possibly reliable, certainly reliable.

In yet another embodiment, the continuous waveform is obtained invasively or non-invasively.

In a further embodiment again, the continuous waveform is inferred from an additional physiological measurement.

In another embodiment again, the other physiological measurement is selected from electrocardiography, photoplethysmography, skin stretch sensor, or electrical impedance or induction.

In a further additional embodiment, the method further includes obtaining an additional physiological measurement as a second continuous waveform, validating a reliability of the second continuous waveform, and outputting a second reliability measure of the second validated waveform reliability.

In another additional embodiment, the additional physiological measurement is selected from the group consisting of electrocardiography, photoplethysmography, skin stretch sensor, or electrical impedance or induction.

In a still yet further embodiment, the continuous waveform is obtained from a clinical monitor.

In a still further embodiment again, a device incorporating a waveform reliability measurement includes a waveform reliability evaluator, a control module, and a fluid pump, where the waveform reliability evaluator receives physiological measurements as a continuous waveform and outputs a reliability measure of the waveform to the control module, where the control module controls infusion rate of the fluid pump based on the physiological measurements and the reliability measure of the waveform.

In still another embodiment again, the fluid pump infuses a cardioactive drug.

In a still further additional embodiment, the cardioactive drug is selected from the group consisting of a blood pressure regulator, a cardiac rate regulator, a cardiac contractility regulator, and a vasomotor tone regulator.

In still another additional embodiment, the cardioactive drug is a vasopressor.

In a yet further embodiment again, the fluid pump infuses a fluid, where the fluid is selected from the group consisting of: a crystalloid, a colloid, and a blood product.

In yet another embodiment again, the continuous waveform is obtained from a clinical monitor.

In yet another additional embodiment, the device further includes a second fluid pump, where the fluid pump infuses a fluid selected from the group consisting of: a crystalloid, a colloid, and a blood product, and the second fluid pump infuses a cardioactive drug.

In a further additional embodiment again, the cardioactive drug is selected from the group consisting of a blood pressure regulator, a cardiac rate regulator, a cardiac contractility regulator, and a vasomotor tone regulator.

In another additional embodiment again, the cardioactive drug is a vasopressor.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

These and other features and advantages of the present invention will be better understood by reference to the following detailed description when considered in conjunction with the accompanying drawings where.

DETAILED DISCLOSURE OF THE INVENTION

The embodiments of the invention described herein are not intended to be exhaustive or to limit the invention to precise forms disclosed. Rather, the embodiments selected for description have been chosen to enable one skilled in the art to practice the invention.

Turning to the data and drawings, systems and methods are provided to assess waveform reliability in blood pressure monitoring. Many embodiments are directed to closed-loop controllers, including controllers designed to correct hypotension and/or hypertension. A number of embodiments correct hypotension and/or hypertension via an automatic titration of an infusion rate of a blood pressure regulator (e.g., a vasopressor) to within a predefined characteristic, such as mean arterial pressure (MAP). Further embodiments infuse a cardiac rate regulator, a cardiac contractility regulator, and/or a vasomotor tone regulator.

Blood pressure control is incredibly important in medical procedures, including surgical procedures, where blood pressure in an individual may fall outside of an acceptable window (e.g., blood pressure is too low or too high). Closed loop systems to infuse blood pressure regulators and/or other cardioactive drugs show a great promise to proactively regulate cardiac parameters (e.g. blood pressure). However, obstructions, interferences, probe locations, and other complicating factors can cause monitoring systems to cardiac parameters can produce variable, inaccurate, and/or untrustworthy readings. As such, many embodiments of the invention are directed to systems and methods to validate waveform reliability from waveforms generated by monitoring devices, such as stroke volume variation (SVV) monitors to improve drug and/or fluid infusion into a patient for better and more accurate control of specific cardiac parameters.

Figure 1A:
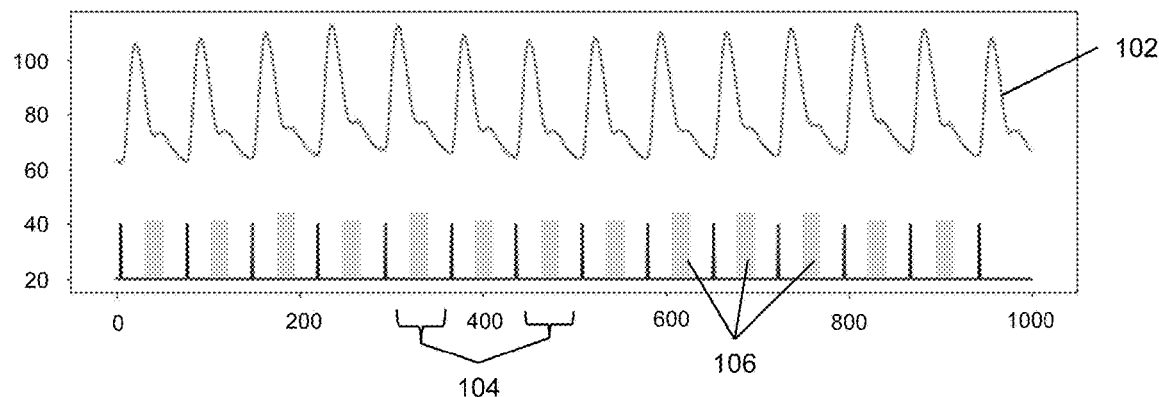
FIGS. 1A-1C illustrate exemplary blood pressure waveforms in accordance with embodiments of the invention.
Figure 1B:
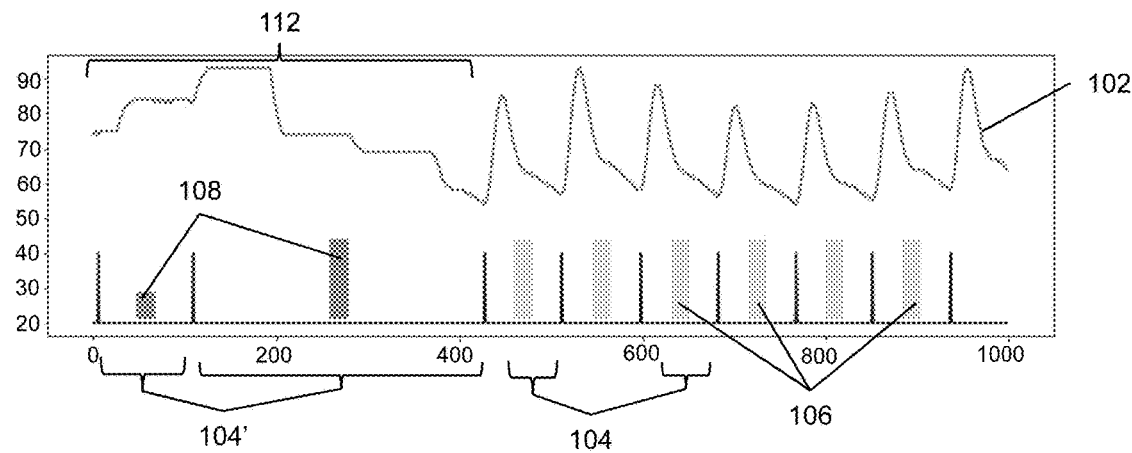
Figure 1C:
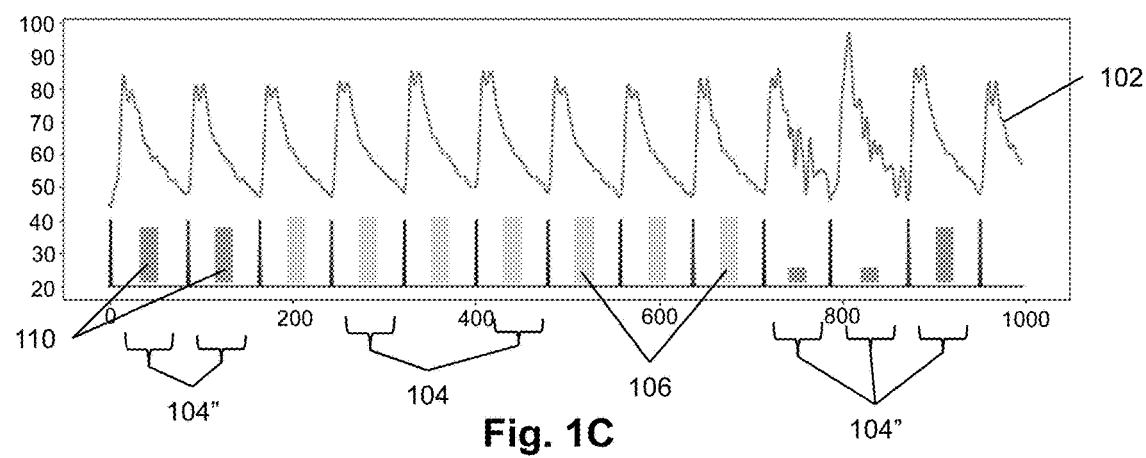

Turning to FIGS. 1A-1C, exemplary waveforms are illustrated. Each of FIGS. 1A-1C illustrate 10-second sections of arterial blood pressure waveforms 102 with beat detection analysis 104, and quality measures 106, 108, 110 of the beats. Beats are generally identified as a time in an arterial waveform between successive diastolic nadirs; effectively the time corresponds to a single cardiac cycle from diastole through systole back to diastole, while quality indicates how "clean" a beat looks.

FIG. 1A illustrates a "good" waveform, while FIGS. 1B-1C illustrate waveforms with poor or bad segments and/or beats. More particularly, in FIG. 1A a clean 10-second section of a waveform 102 is illustrated with fourteen beats 104, all of which have a "good" quality measurement 106. FIG. 1B illustrates a 10-second section with a segment 112 having a bad signal, which can be caused by compression of an artery and/or measurement line. While two beats 104' are identified within segment 112, both show "bad" quality measurements 108 for having bad beat morphology. Finally, FIG. 1C illustrates readily visible beats 104, however several beats 104" illustrate artifactual noise as oscillations in the waveform 102. While these oscillatory beats are correctly identified morphologically, the beats are identified as "poor" quality 110 due to the oscillations in waveform 102.

Embodiments Implementing Methods and Systems for Identifying Waveform Features

To identify beats within waveform data, various embodiments filter incoming signals, such as those coming from blood pressure monitors and/or other physiological measurements, such as through the use of a lowpass filter. Additional embodiments further perform one or more of Fourier transformation to detect dominant time constants, selection for probable heart rate peaks, and scanning of a waveform for peaks and troughs within a specified frequency. In certain embodiments, probably heart rate peaks are determined by peaks occurring in a range of 30-130 Hz. Further embodiments provide a higher weighted probability given to values near the middle of the 30-130 Hz range.

Figure 2A:
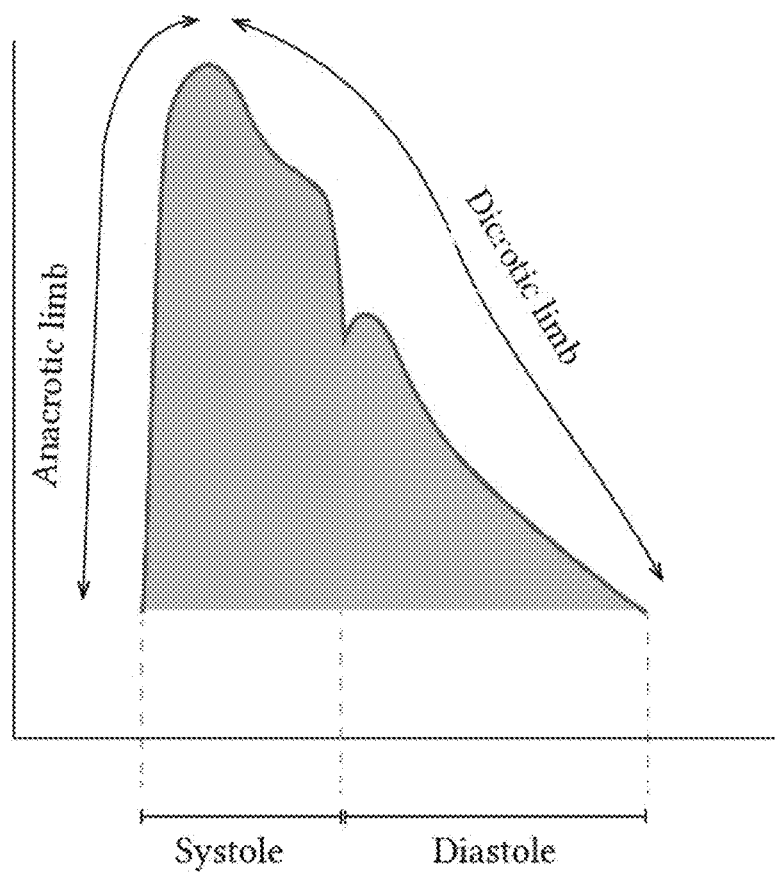
FIGS. 2A-2B illustrate general waveform characteristics in accordance with embodiments of the invention.
Figure 2B:
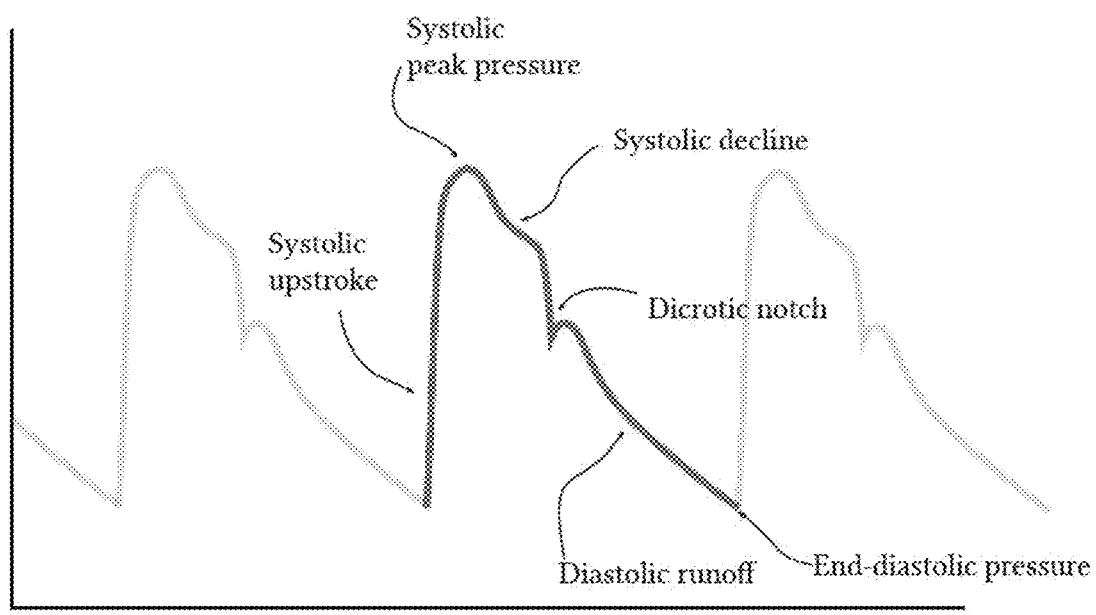

Turning to FIGS. 2A-2B, general waveform characteristics are illustrated relative to a single beat. In particular, FIG. 2A illustrates portions of a waveform that represent systole and diastole as well as the anacrotic and dicrotic limbs in a single beat. FIG. 2B illustrates a little more granularity within a beat waveform, identifying the systolic upstroke, peak pressure, and decline as well as dicrotic notch, diastolic runoff, and the end diastolic pressure.

In addition to the features identified in FIGS. 2A-2B, a number of embodiments identify and measure or calculate a variety of additional feature within a single beat's waveform. Waveform features are generally categorized into one of the following categories:

Pressures—direct measures of the blood pressure at a given time point in the pressure wave, typically measured in millimeters of mercury (mmHg). For example, systolic blood pressure, diastolic blood pressure, and blood pressure at 30% of the time between the systolic peak and the end of the beat, among others.

Pressure Ratios—ratios of two pressures relative to one another. For example, systolic blood pressure divided by diastolic blood pressure, among others.

Time—typically direct measurements of the times of features in the beat. For example, time from beat start to systolic blood pressure, time from beat start to 50% fall in systolic peak relative to diastolic nadir, time from 50% rise in pressure upslope to 50% fall in pressure downslope, and time from systolic peak to dicrotic notch peak if present, among others.

Time Ratios—ratios of two times relative to one another. For example, total systolic time to total beat time, and time between 50% rise in systolic upslope and systolic peak to time between systolic peak and 50% downslope pressure, among others.

Area—The sum of all measures in all or a portion of the wave. For example, total area under the beat, total area under the beat minus total diastolic area, and total area under the 75th percentile of systolic pressure, among others.

Slope—the rate of change of the pressure wave at a point in the wave. For example: rate of rise in the first quintile of systolic upslope, rate of rise of the total systolic upslope, and rate of fall in the third quintile of systolic downslope, among others.

Morphology—Detection of specific features when present or not (often binary "yes" or "no"). For example, presence of a double-systolic peak, and presence of more than two beat peaks, among others.

Table 1 lists a number of the features, including category, an abbreviation for the feature, the feature name and description, units for the feature, and how each feature is measured and/or calculated in accordance with many embodiments.

While the features listed in Table 1 exemplify certain features that may be specific to arterial blood pressure waveforms, the general categories of waveforms, including areas, time ratios, pressure ratios, peaks, morphologies, etc. are applicable to many types of waveforms, including other physiological measurements, including (but not limited to) neural monitoring, electrocardiography (e.g., ECG/EKG), pulse oximetry, central blood volume, central blood flow, photoplethysmography, skin stretch sensor, other light transmittance or reflectance measurements to detect blood flow, other electrical impedance or induction measurements measuring blood volume. As such many embodiments perform similar techniques, such as described herein, to such physiological measurements. Furthermore, non-physiological measurements (e.g., temperature and/or pressure controls) may also produce continuous waveforms to which embodiments are directed in order to identify changes in non-physiologic measurements and control.

Figure 3A:
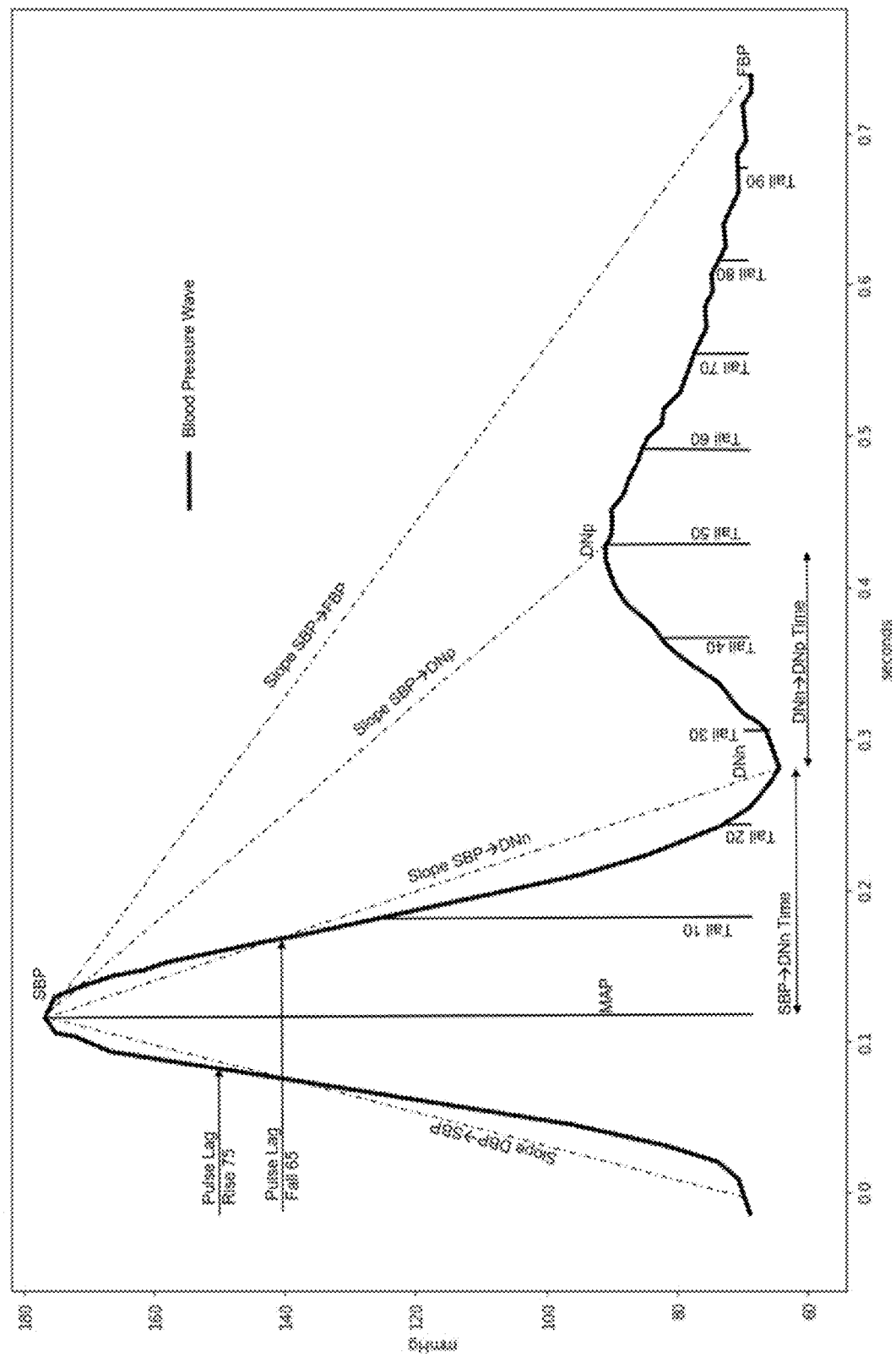
FIGS. 3A-3F illustrate features that can be extracted from a single beat waveform in accordance with embodiments of the invention.
Figure 3B:
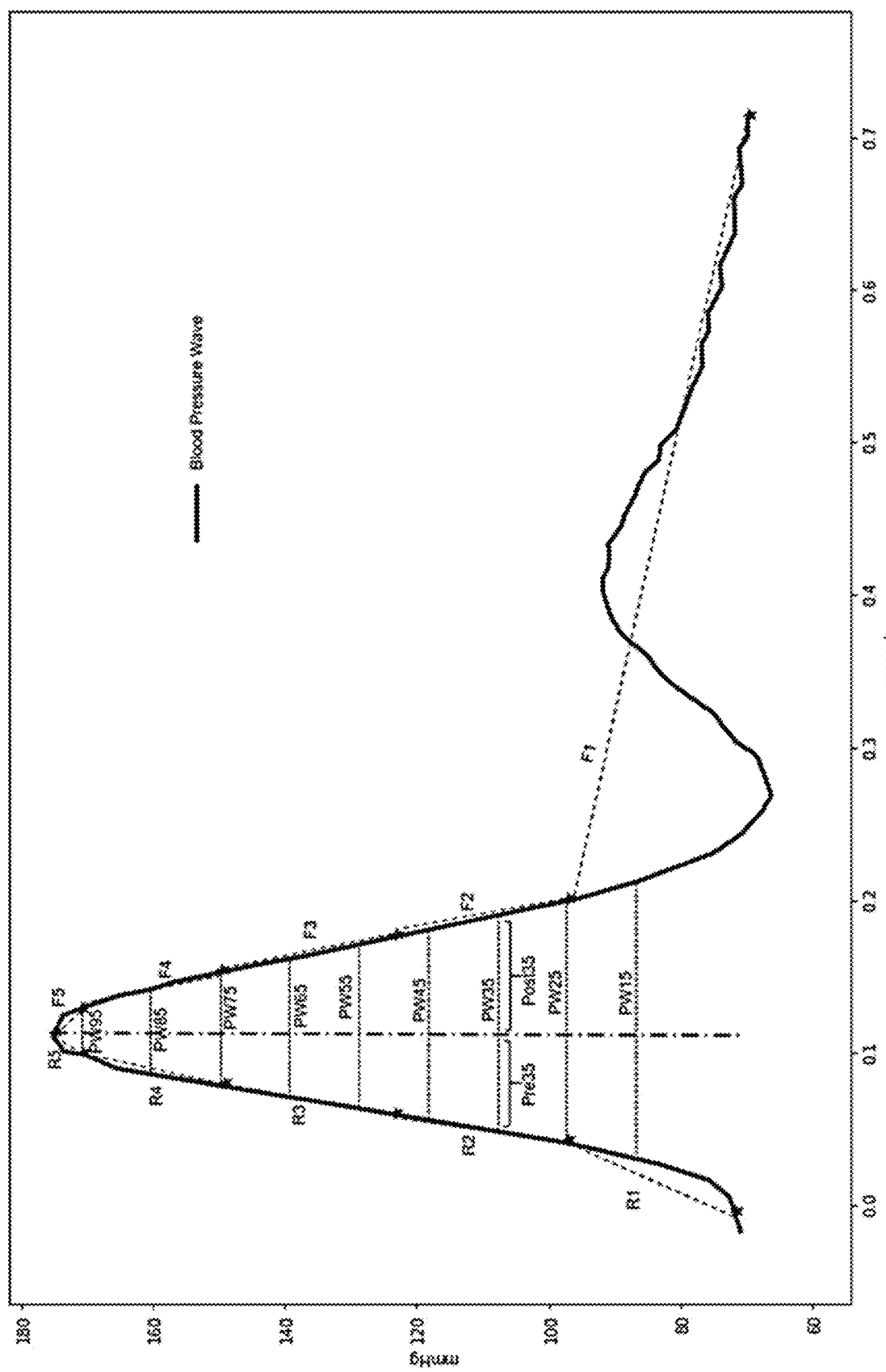
Figure 3C:
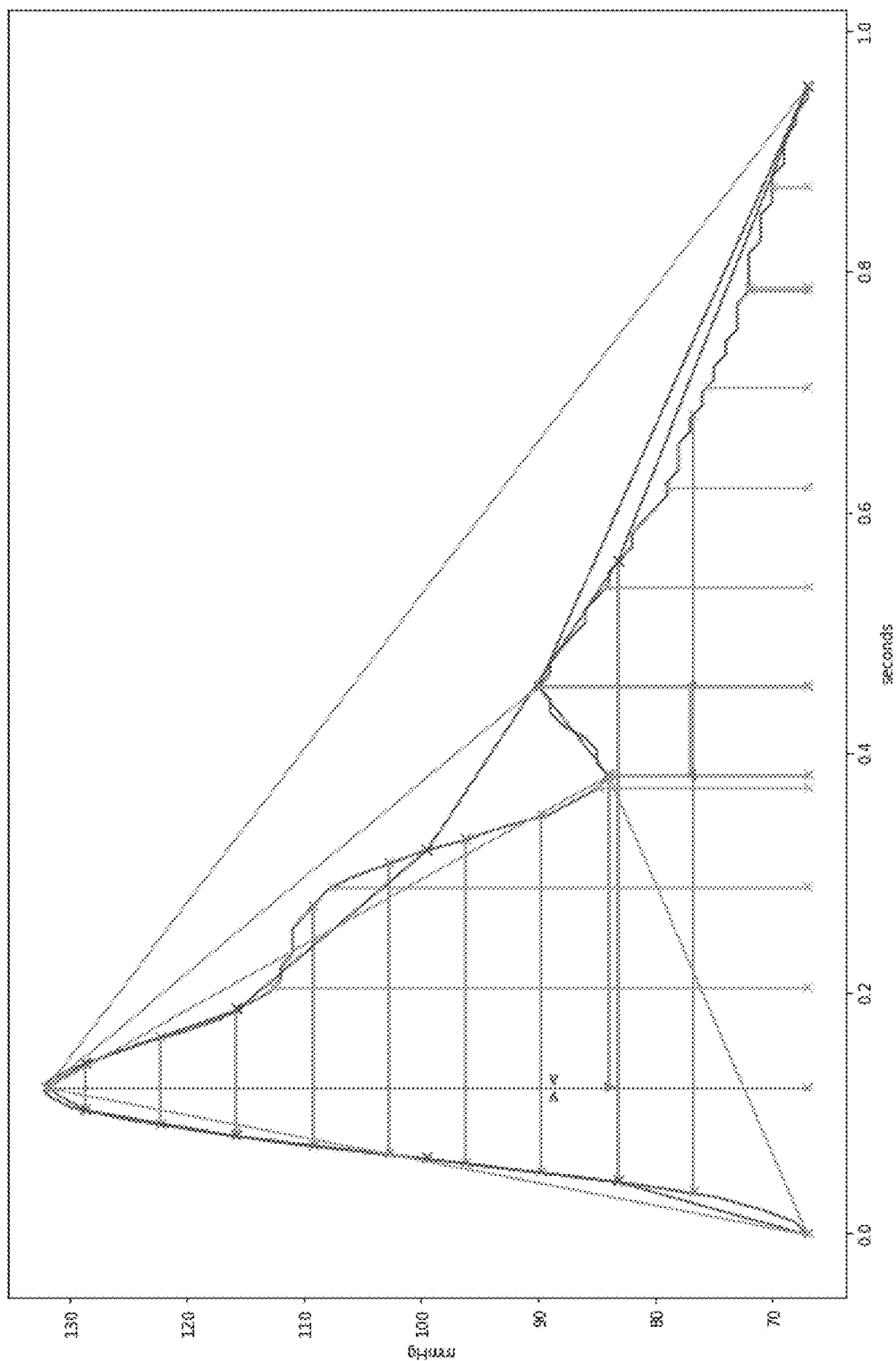
Figure 3D:
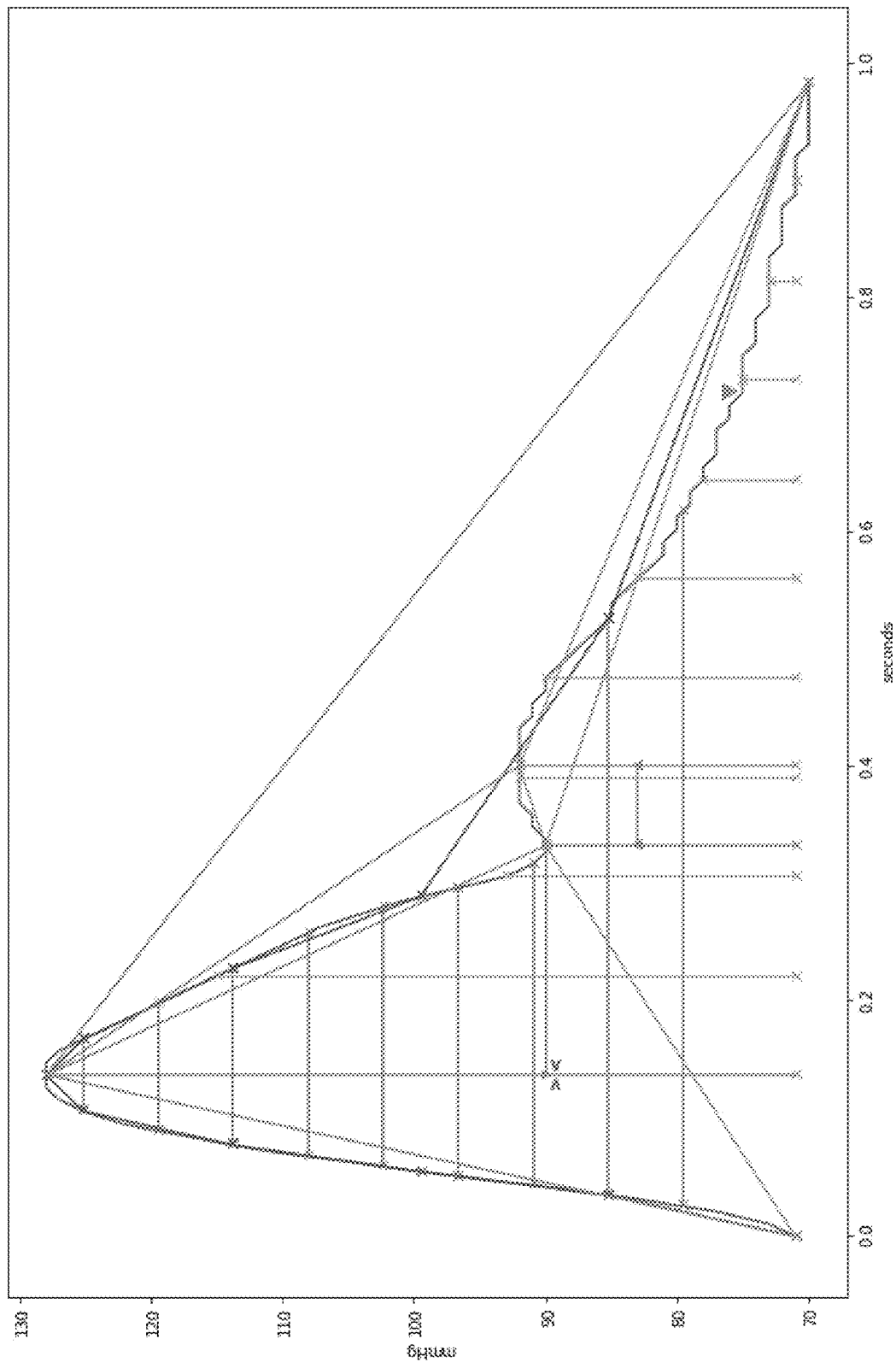
Figure 3E:
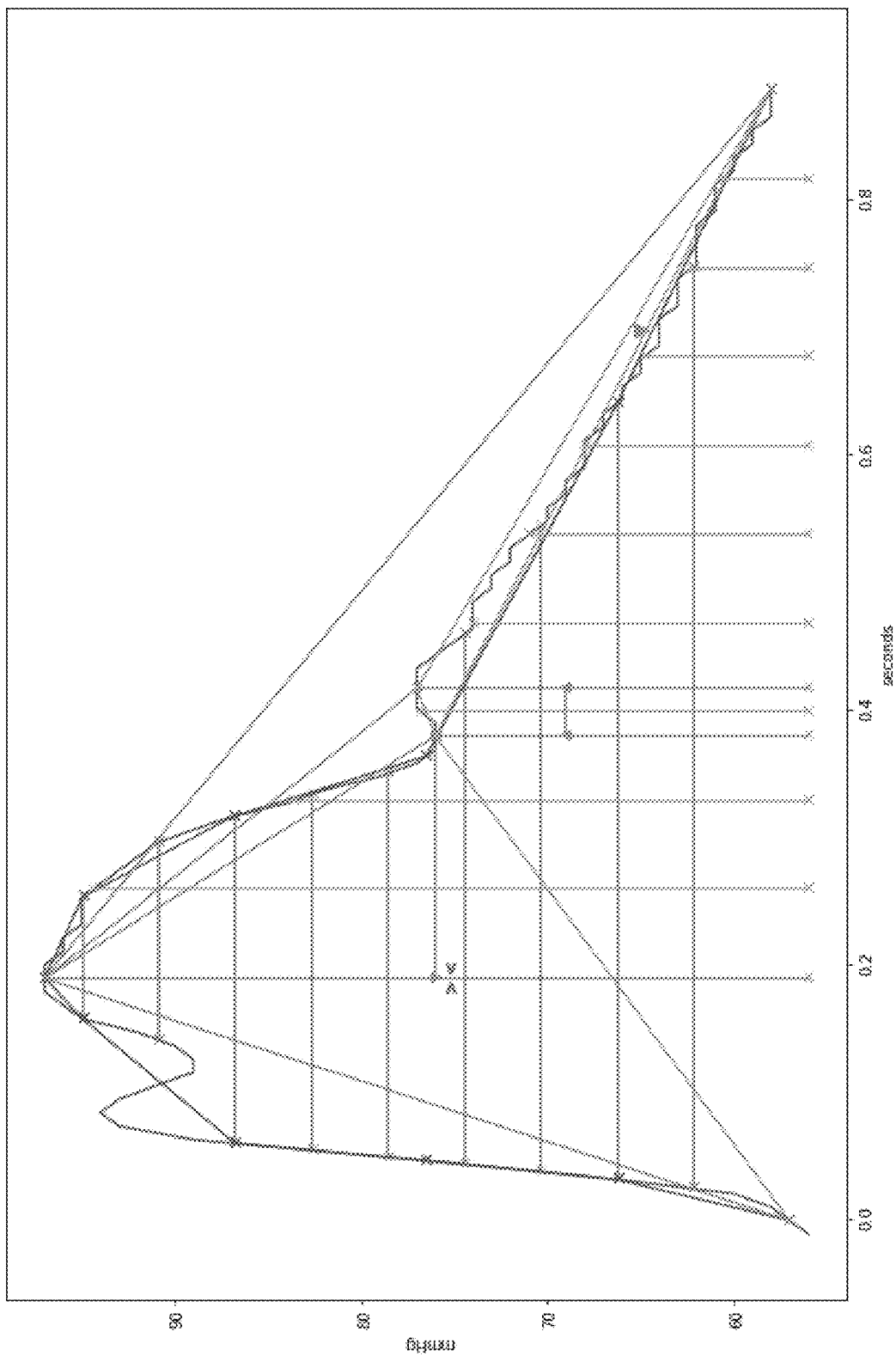
Figure 3F:
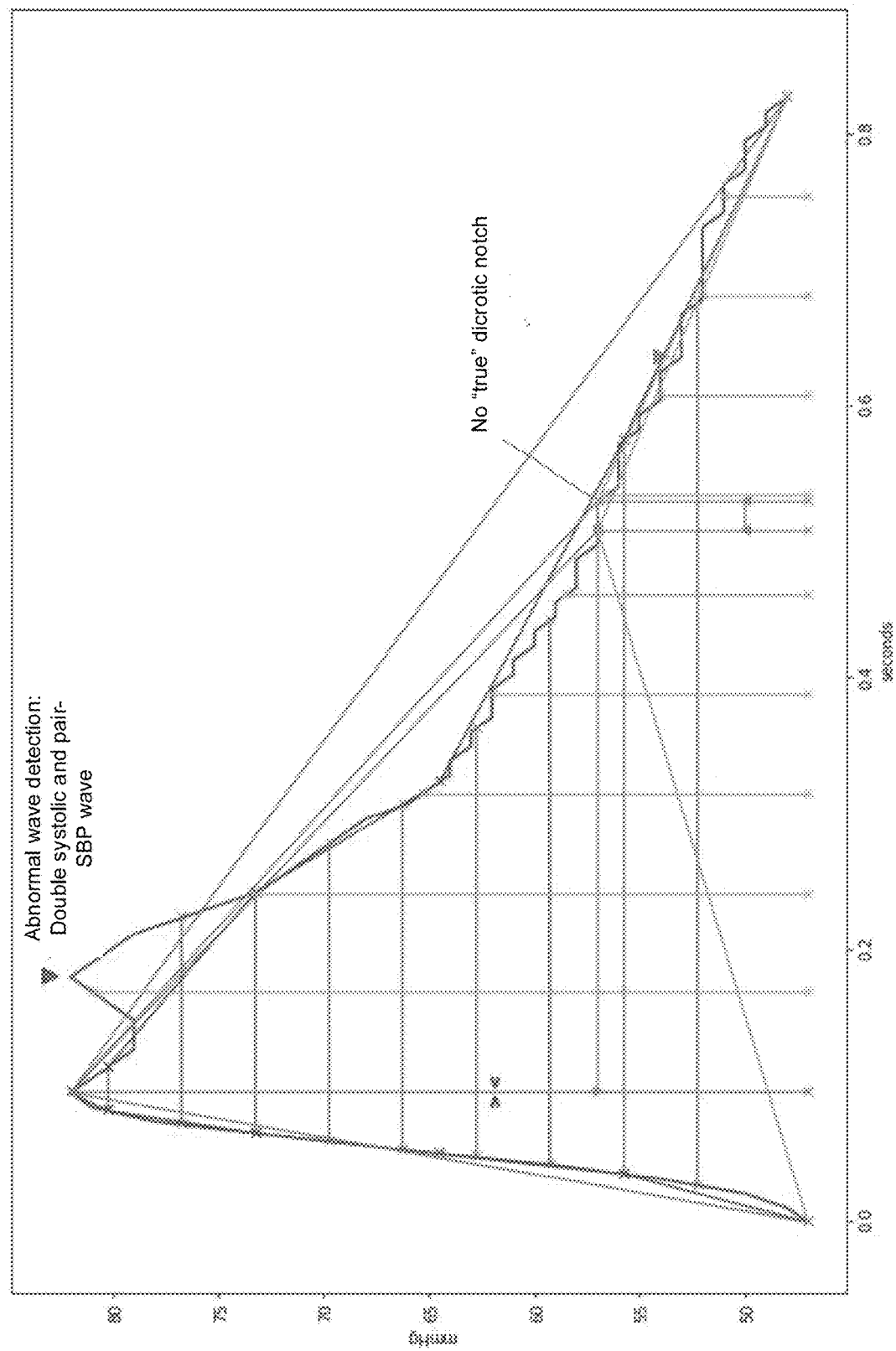

Turning to FIGS. 3A-3F, a number of the features that can be identified and measured or calculated are illustrated against the morphology of a single beat. In particular, FIGS. 3A-3B illustrate a single beat with a deep notch and reflection wave, where a number of extractable features (e.g., features from Table 1) are drawn and labeled, including pressures, times, slopes. FIGS. 3C-3E illustrate the same measurements as shown in FIGS. 3A-3B on different beats with different morphologies, such as a lagging shoulder on the systolic peak (FIG. 3C), shallow dicrotic notch (FIG. 3D), or multiple systolic peaks (FIG. 3E). Finally, FIG. 3F illustrates an abnormal waveform with a double systolic peak and no "true" dicrotic notch, thus no "true" second (or dicrotic) peak. Because of the abnormality in FIG. 3F, this figure illustrates how certain embodiments extract features in abnormal waveforms. Specifically, FIG. 3F illustrates how maximum concavity of the downslope can first be detected, followed by identification of the maximum positive deflection from the line connecting the maximum concavity to the end of the beat, in order to identify certain features for extraction.

Many embodiments identify and/or measure (or calculate) one or more of the various features discussed herein (e.g., the features listed in Table 1) for one or more models. For example, Table 2 lists features used in exemplary models for detecting arterial line transducer is too high, detecting arterial line transducer is too high, and detecting dampening, in accordance with various embodiments. Further embodiments determine median values for one or more features, variance in one or more features, changes in one or more features (e.g., changes in the features between beat waveforms), and/or the change in variance of one or more features. A number of embodiments combine one or more of these four categories of measurements for different uses, such that certain embodiments only measure one or more of the features alone, while additional embodiments measure one or more features and the variance in these features over a period of time or beats (e.g., 60 seconds and/or 60 beats). Additional embodiments measure only the change in measurements over a period of time or a number of beats (e.g., 60 seconds and/or 60 beats), such that the change over time is identified. Numerous other embodiments combine a selection of these categories, such that the embodiments measure one or more features, variance in the measurements, change in the measurements over a period (e.g., 60 seconds), and change in variance over a period (e.g., 60 seconds). Further embodiments use a large set of instant and change measurements covering different periods. For example, these embodiments could measure one or more features; variance in one or more features; change in measurements over 60 seconds, 180 seconds, and 900 seconds; and change in variance over 60 seconds, 180 seconds, and 900 seconds. Variance in some embodiments is calculated as ($75^{th}$ quantile value)–($25^{th}$ quantile value).

Certain embodiments normalize data for some features, including, for example, heart rate and mean arterial pressure, which affect other features. Normalization may include correction for natural variation of measured features over the span of heart rate and mean arterial pressure. For example, the diastolic time in a typical sinus rhythm is long when the heart rate is low, and short when the heart rate is high. Moreover, the curve of the graph of diastolic time (y-axis) by heart rate (x-axis) is non-linear (e.g., it exhibits a curvature). Thus, in the processes of vetting various normalizations of all of the features against either heart rate or mean arterial pressure, polynomial regression is employed in various embodiments to best fit the natural variation to normalized values for the given heart rate or mean arterial pressure range.

It should be noted that specific times or periods identified in these exemplary embodiments are for illustration purposes only, such that identifying a period of 60 seconds could be 15 seconds, 30 seconds, 45 seconds, 120 seconds, or any other period of time. Similarly, identifying 60 beats could further be further adjusted as a period of 15 beats, 30 beats, 45 beats, 120 beats, or any other number of beats that would be useful for obtaining these measurements. Additionally, a number of embodiments measure changes or changes in variance of periods (either time or number of beats) as discrete windows (e.g., period 1 measures change from 1-60 seconds, period 2 measures change from 61-120 seconds, etc.), while further embodiments measure changes or changes in variance of periods over a sliding window (e.g., period 1 measures change from 1-60 seconds, period 2 measures change from 16-75 seconds, etc.).

Embodiments Implementing Training Waveform Reliability Algorithms

Many embodiments are directed to validating waveform reliability of blood pressure measured from an individual. Waveform reliability refers to whether a waveform is an accurate representation of an individual's blood pressure. As identified herein, a number of embodiments utilize automated algorithms, including machine learning and/or artificial intelligence algorithms to validate waveform reliability by identifying features from a waveform, such as those features described herein. Once a model is trained, many embodiments validate the model using a validation dataset. Once validated, trained models of certain embodiments be used to validate waveform reliability.

Many embodiments train a model using a supervised approach to learning by being taught using valid and good quality beat waveforms (e.g., item 104 in FIGS. 1A-1C) and omitting bad and/or poor beat waveforms (e.g., items 104' and 104" in FIGS. 1A-1C). Further embodiments use one of unsupervised, semi-supervised, or reinforcement learning; however, these methodologies may train a model incorrectly without a pre-validated training set.

Numerous embodiments use model-based learning to identify valid waveforms and validating waveform reliability based on features within the waveforms, including variance, change, and change in variance of these features. While certain embodiments may use instance-based learning, models trained using instance-based learning may not be as effective due to a "lazy" learning methodology.

Certain embodiments use a neural network approach, including one or more of deep learning, convolutional, and/or recurrent subtypes, such that certain embodiments use one type of neural network, while some embodiments use an ensemble approach to learning for the neural network. Additional embodiments can use support-vector, regression modeling, or linear modeling to train the machine learning algorithm, which may be effective given pre-validated waveform data. Further embodiments may use decision trees, k-nearest neighbors, and/or binary classifiers; however, these models may not be as effective given waveform data in embodiments.

Further embodiments incorporate additional information about the validated waveform that may affect waveform reliability in certain individuals. The additional information can include characteristics including age, disease state, disease severity, location of blood pressure measurements, and/or any other characteristic that may affect blood pressure, blood flow, and/or blood volume within the individual.

Disease states and/or severity include such characteristics as diabetes I & II, peripheral vascular disease, peripheral arterial disease, cardiac disease (e.g., myocardial infarction history, congestive heart failure, aortic & mitral valve pathology, regurgitation, stenosis, etc.), pulmonary hypertension, vasodilatory shock states (including sepsis, neurogenic, and/or vasoplegic shock states), carotid stenosis, and/or any other disease state or severity that may affect blood pressure, blood flow, and/or blood volume. Measurement locations include such femoral, radial, brachial, pedal, and/or central measurement locations. By incorporating datasets including these additional pieces of information, the trained model in certain embodiments may provide better accuracy in validating waveform reliability in individuals of certain ages, diseases, and/or the location of the specific blood pressure measurements in the individual.

In certain embodiments, training data is collected among normal states (e.g., no error) and/or one or more states, including transducer high, transducer low, dampened states, and/or any other known error states. A transducer place too high (transducer high) is sufficient to cause a 10-12 mmHg drop in MAP, while a transducer placed below a patient (transducer low) is sufficient to cause a 10-12 mmHg rise in MAP. Dampened states can be caused by air or another gas introduced into an arterial blood pressure fluid line, which causes dampening of a waveform signal.

Various embodiments calibrate data based on normal (e.g., non-error) data for an individual from which the data is collected. For example, if the median pulse-pressure in the calibration frame period was 50 mmHg, and at some future state the pulse-pressure was 40 or 60, those values would be recalculated as change from baseline of −10 and +10 respectively in the calibrated dataset.

Some embodiments train an algorithm for multi-class detection, such that the algorithm is capable of detecting multiple error states. However, numerous embodiments train separate algorithms for each error state, which may allow for better focusing of training for the specific type of error.

Various embodiments expand features through transformation and/or combination, where transformation can be selected one or more of natural log, square, reciprocal, or any other transformation method as relevant for heart rate data. Certain embodiments assess prediction of the error state under consideration using a mutual information classifier, where the highest mutual information score for any single base feature can be identified and set as a cutoff value for transformed feature detection. In certain embodiments, once a cutoff value is accepted, each of the base features is sequentially tested as raw measurement or as transformed measurement individually and then in combination with every other feature, itself both raw and transformed. Combinations in various embodiments include sums, differences, absolute differences and sums, ratios, and products. Additional embodiments retain any combined feature with a mutual information score higher than the cutoff.

Following feature expansion, many embodiments establish a Monte-Carlo feature selection and machine-learning training pipeline. For feature selection, certain embodiments use a "K-Best" selector with an f-classifier to select the features with the strongest relationships to the error state of interest. Various embodiments select machine learning classifier algorithms from the group consisting of: Linear Regressor, Ridge Regressor, Perceptron, Passive-Aggressive Regressor, Decision Trees, Support Vector Machines, K-Nearest Neighbors, Stochastic Gradient Descent, and Multilayer Perceptron neural net.

Various embodiments select a machine learning algorithm by selecting a random number of K-best features, one of the above listed machine learning algorithms, and then choose from a randomized subset of available hyper-parameters for the machine learning algorithm (if any). Various embodiments then check the balanced accuracy of each trained algorithm in the training set using 10-fold cross-validation within the training set; where balanced accuracy is simply accuracy (number of correct predictions divided by the total number of observations) balanced for the number of observations obtained on each individual class.

Algorithm testing and selection in various embodiments includes allowing the selection pipeline to run numerous samples (e.g., 10,000 samples), then consistently, highly performing algorithms are allowed to re-run algorithm selection to determine the best algorithm for each error state. Additional algorithms are selected in some embodiments based on calibrated and uncalibrated data.

Figure 4A:
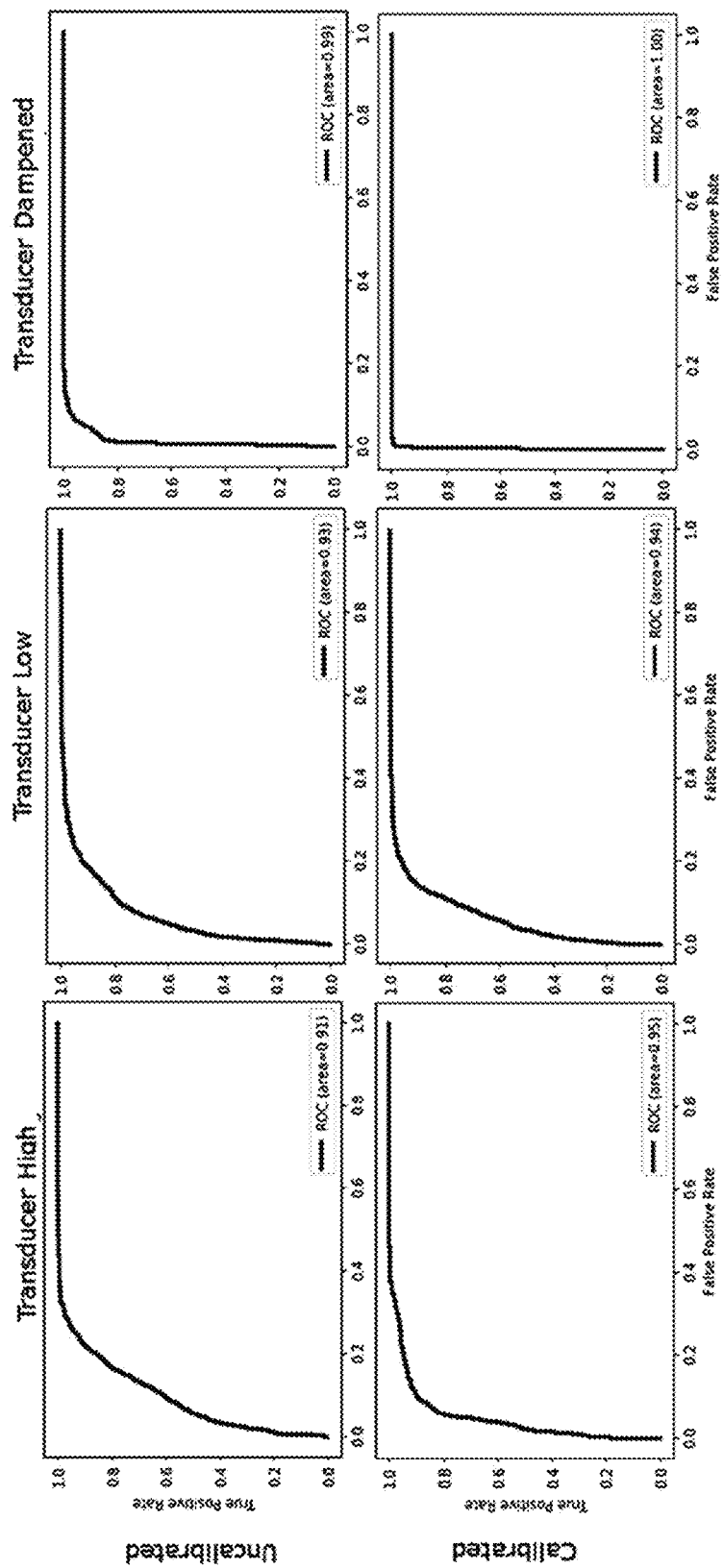
FIGS. 4A-4B illustrate receiver-operator curves and precision-recall curves in accordance with embodiments of the invention.
Figure 4B:
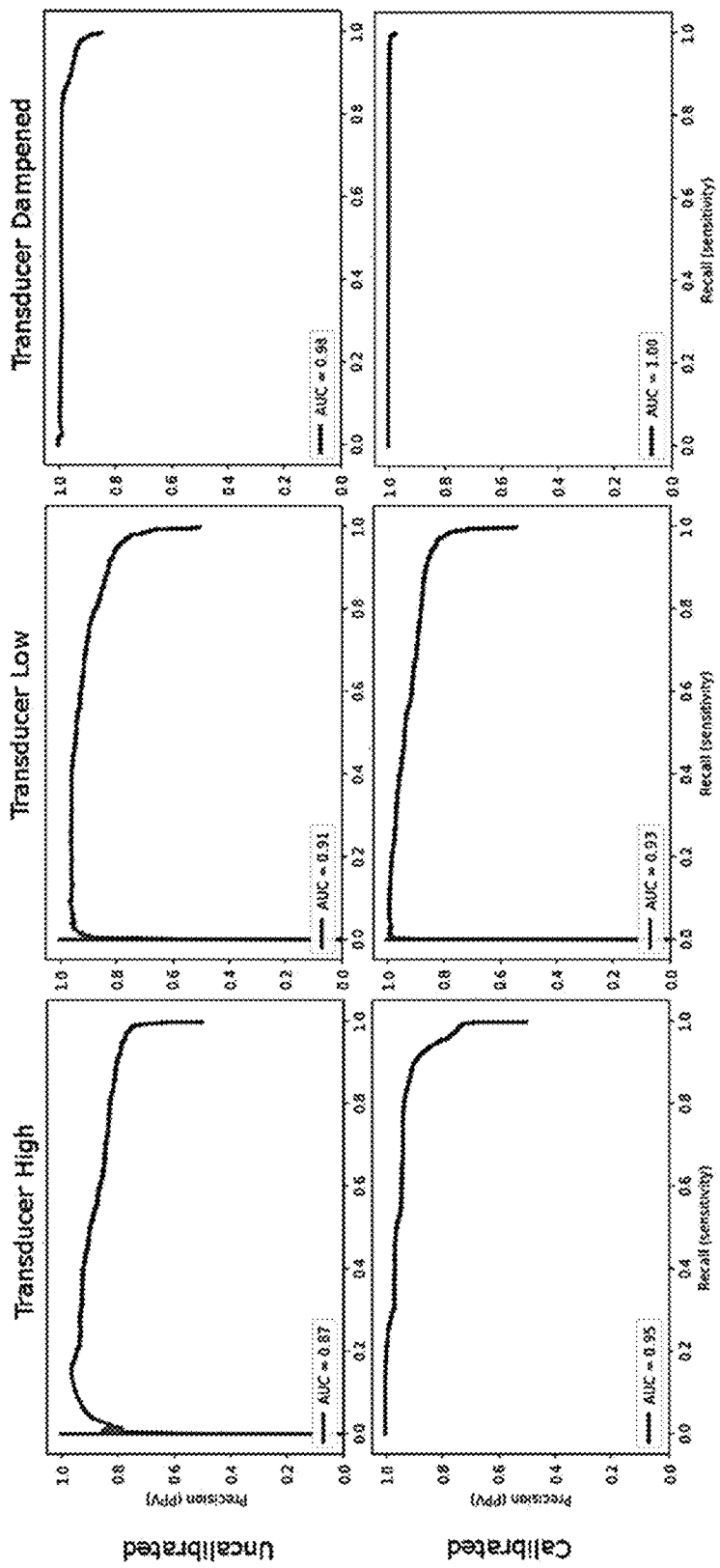

Once machine learning algorithms are selected, the algorithms are tested against additional data. FIG. 4A illustrates receiver operating characteristic curves from embodiments illustrating each error state using calibrated or uncalibrated data, where these embodiments are capable of achieving an area under the curve (AUC) of 0.90 or greater. FIG. 4B illustrates precision-recall curves for the three error states using calibrated or uncalibrated data. Precision is defined as true positives/(true positives+false positives), and recall is defined as true positives/(true positives+false negatives). FIG. 4B illustrates that PRC AUC achieved in these embodiments is 0.87 or greater.

Validating Waveform Reliability

Figure 5:
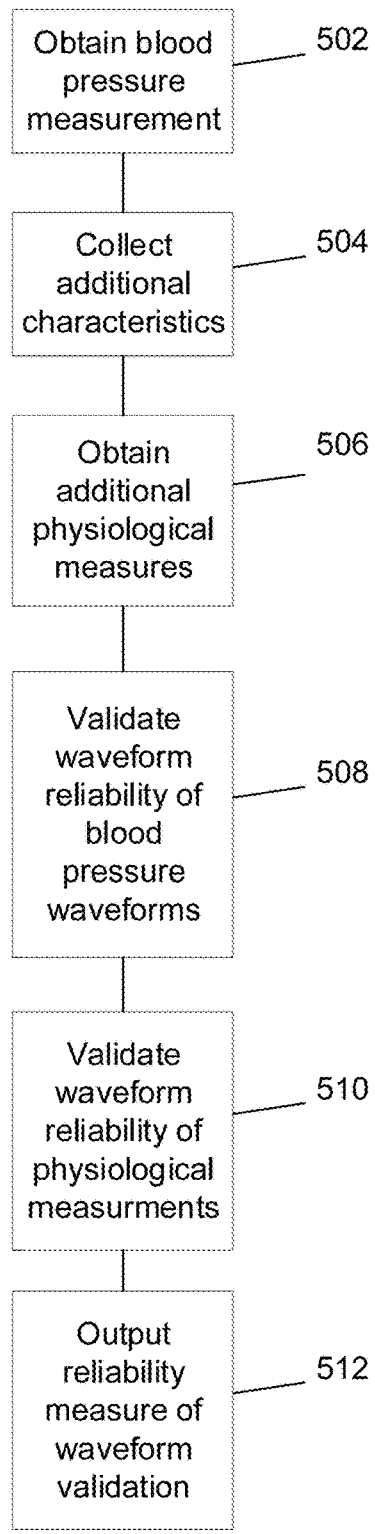
FIG. 5 illustrates a flow chart of a method for validating blood pressure measurements in accordance with embodiments of the invention.

Turning to FIG. 5, a method 500 of validating blood pressure measurements is illustrated. In a number of embodiments, a blood pressure measurement of an individual is obtained at step 502. In some embodiments a blood pressure waveform measurement is obtained invasively (e.g., via a transducer), while some embodiments obtain a blood pressure waveform measurements non-invasively, such as a non-invasive transducer or pressure measurement. Certain embodiments obtain a blood pressure measurement using a clinical monitor and/or any other suitable monitoring device. Certain embodiments obtain blood pressure measurements as a continuous waveform, such as those illustrated in FIGS. 1A-1C. A number of embodiments obtain multiple blood pressure measurements from the individual from additional sensors and/or monitors connected to different parts of the individual's body.

Some embodiments collect additional characteristics about the individual and/or measurements, such as age, disease state, disease severity, location of blood pressure and/or other physiological measurements, and/or any other characteristic that may affect blood pressure, blood flow, and/or blood volume within the individual at step 504. Characteristics or information from the individual, such as age, disease state, etc., may affect shape of a waveform morphology, thus certain embodiments collect additional characteristics about the individual.

At step 506 of many embodiments, other physiological measurements are obtained from an individual. In certain embodiments, other physiological measurements from electrocardiography (EKG/ECG), pulse oximetry, central blood volume, central blood flow, photoplethysmography, skin stretch sensor, other light transmittance or reflectance measurements to detect blood flow, other electrical impedance or induction measurements measuring blood volume, and/or any other physiological measurement tied to blood flow and/or blood volume are obtained. A number of these other physiological measurements are captured as continuous waveforms, similar to those for blood pressure. In some of these embodiments, the other physiological measurements may allow inference of a blood pressure waveform measurement.

At step 508, many embodiments validate waveform reliability of blood pressure waveforms. Numerous embodiments validate waveform reliability using a model trained via a machine learning algorithm. A number of embodiments include additional characteristics about the individual (e.g., characteristics collected at Step 504) to validate waveform reliability. Methods of training and validating models are described elsewhere herein.

At step 510, several embodiments validate waveform reliability using other physiological measurements (e.g., measurements obtained at Step 506). Certain physiological measurements, such as EKG, produce waveforms that can be validated similarly to blood pressure waveforms, including the use of machine learning algorithms trained with EKG measurements correlated to blood pressure waveforms may be used. Certain other physiological measurements, such as pulse oximetry, may be usable directly as predictors of blood pressure.

In a number of embodiments, waveform reliability from at least one of Step 508 and Step 510 are output at step 512. In certain embodiments the output is a qualitative measure and/or binary identifier, such as "reliable" or "not reliable." Additional embodiments output a quantitative identifier of reliability, such as a such as a continuous confidence measure of reliability (e.g., 0%-100% confidence). Further embodiments output semi-quantitative identifiers of reliability, such as an ordinal confidence measure (e.g., not reliable, possibly reliable, certainly reliable).

Embodiments Implementing Devices Incorporating Waveform Reliability Measures

Figure 6:
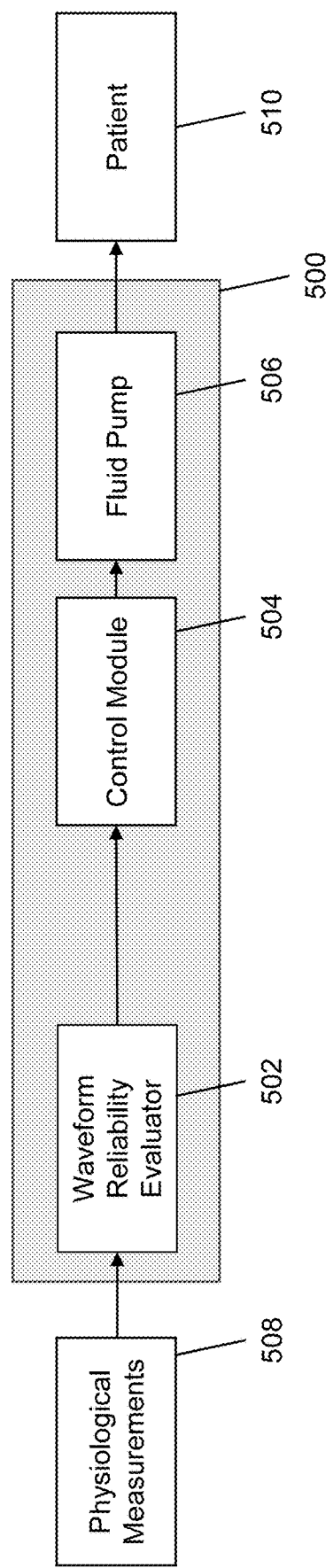
FIG. 6 illustrates a device incorporating a waveform reliability measures in accordance with embodiments of the invention.
Figure 7:
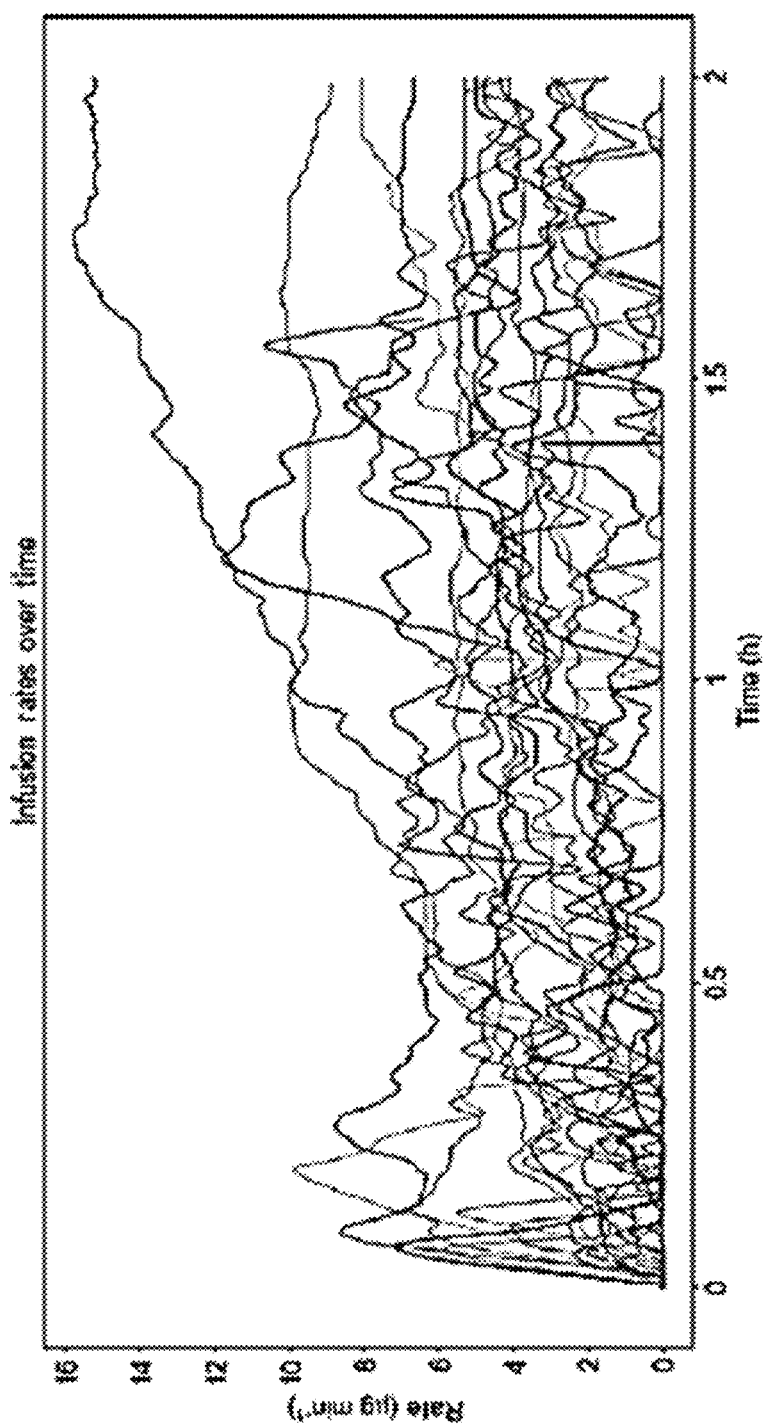
FIG. 7 illustrates norepinephrine infusion rate over time for multiple individuals being monitored with a closed loop system in accordance with embodiments of the invention.

A variety of embodiments are directed to devices incorporating waveform reliability information. Some of these devices are life-supporting devices, while others are life-sustaining devices. Turning to FIG. 6, an embodiment of a drug delivery system 500 in accordance with various embodiments is illustrated. A drug delivery system 500 in accordance with certain embodiments include a waveform reliability evaluator 502, a control module 504, and at least one fluid pump 506. In many embodiments, the waveform reliability evaluator 502 receives physiological measurements 508 from a physiological monitor. Physiological measurements 508 include one or more of blood pressure waveforms, EKG waveforms, and/or any other physiological measurement (e.g., physiological measurements discussed in relation to FIG. 4 and its associated text). In many embodiments the waveform reliability evaluator 502 evaluates waveforms in accordance with method 400 described herein. A number of these embodiments include a machine learning system to evaluate waveform reliability, trained according to systems and methods described herein.

Output from a waveform reliability evaluator 502 (e.g., quantitative, qualitative, and/or semi-quantitative) is sent to a control module 504 along with the physiological measurements, in various embodiments. In certain embodiments, the control module 504 includes an input and/or output interfaces. Numerous embodiments allow a medical professional (e.g., nurse, physician, surgeon, etc.) to input control parameters into the control module 504, where control parameters include a target parameter, target range, and/or certain rules. For example, a number of embodiments allow a medical professional to input a target blood pressure and/or target blood pressure range (e.g., 70-80 mm Hg and/or 75±5 mm Hg), and certain embodiments allow a medical professional to input maximum and/or minimum infusion rates. Various embodiments allow a medical professional to adjust and/or override target parameters (e.g., target blood pressure) during an operation or procedure in which the control module 504 is being used.

Several embodiments allow the control module 504 to filter incoming data (incoming physiological measurements 510 and/or input from a medical professional) for aberrant values. The control module 504 in many embodiments allow for calculation of trends, moving averages, derived values, and/or calculations of potential future states (e.g., predicted values). Certain embodiments allow for storage of data within the control module 504.

Numerous embodiments with a control module 504 control fluid infusion rate from at least one fluid pump 506. In certain embodiments, the control module 504 is a closed loop controller that automatically adjusts a flow rate of the at least one fluid pump 506 based on the physiological measurements 508. In some embodiments, multiple control modules 504 may be used, where each control module 504 controls a single fluid pump 506—for example one control module 504 controls a first fluid pump 506 to deliver a fluid (e.g., crystalloids, colloids, blood products, etc.), while a second control module 504 controls a second fluid pump 506 to infuse a drug (e.g., a vasopressor). Further embodiments utilize a single control module 504 to control multiple fluid pumps 506, such that the one control module 504 can control a first fluid pump 506 to deliver a fluid and a second fluid pump 506 to infuse a drug. Fluids and/or drugs infused from the at least one fluid pump 506 are infused into a patient 510.

In certain embodiments using multiple control modules 504, the control modules communicate or coordinate between each controller to allow for preferences for fluid, drug, or balanced treatment. Such preferences can be set by a medical professional. Table 3 lists an exemplary decision matrix for a preferential system and how the drug delivery system acts depending on vasopressor state and preference. Alternatively, in a closed loop fluid controller ("CLF") model, a direct decision matrix can be used. Table 4 lists an exemplary matrix for an alternate CLF model based on stroke volume variation and mean arterial pressure readings from an individual. It should be noted that the decision matrices in Tables 3 and 4 are exemplary for specific embodiments and one of skill in the art would understand how to manipulate decision matrices depending on preferences and/or readings depending on the specific fluid and/or drug being infused.

Certain embodiments allowing the setting of various rules of operation of the control module 504. For example, some embodiments allow a medical professional to set up a "wean" mode and/or a "ramp" mode, such that infusion rates can be tapered up or tapered down gradually to meet a certain target and/or infusion rate. In additional embodiments, the control module 504 allow for decision support, such that during certain physiological phenomenon, particular infusion methods and/or rates are specifically implemented—for example, a higher fluid infusion rate may be implemented, if a low stroke volume is indicated in the physiological measurements 508. Further embodiments implement machine learning methodologies within a control module 504 to allow proactive control when a certain physiological state is predicted. Additional embodiments allow for control using a proportional integral derivative (PID) module, where a PID element allows for adjustment of both current and anticipated future error.

Features that exist in further embodiments of control modules 504 include alarms, alerts, and/or network interfaces. Alarms and/or alerts can be any suitable method of alerting a medical professional of an issue with physiological measurements 508 and/or operation of the drug delivery system 500, including audible, visible, and/or tactile alerts. Network interfaces implemented in certain embodiments allow for remote operation, remote monitoring, and/or updating underlying software, firmware, and/or parameters of the control module 504, including if improvements to any utilized machine learning model occur to better operate the control module 504. In certain embodiments, an alarm is based on duration of error. For example, various embodiments set a threshold of time outside of a target range, such that an alarm alerts (audible sound and/or visual signal) after a certain amount of time passes outside of the target range. Various embodiments allow for the time outside of the threshold to be adjusted manually, while some embodiments automatically set an alarm time based on specific circumstances of the individual (e.g., age, health, etc.). Some embodiments allow for a warning signal to occur once the parameter exceeds the target range, and an alarm signal to occur once the threshold has been exceeded for a period of time. Additionally, further embodiments provide similar warnings and/or alarms based on the deviation outside of a target range. For example, once a deviation exceeds the threshold, a warning alerts and an alarm alerts after the parameter exceeds an additional threshold. Additional embodiments provide a hybrid approach, such that a combination of deviation size and time outside of threshold are utilized to for an alarm. For example, smaller deviations may allow a longer time outside of the target range before an alarm occurs, while a larger deviation triggers an alarm in a shorter amount of time.

EXEMPLARY EMBODIMENTS

Although the following embodiments provide details on certain embodiments of the inventions, it should be understood that these are only exemplary in nature, and are not intended to limit the scope of the invention.

Example 1: Testing a Closed-Loop Vasopressor System

BACKGROUND: A closed-loop system in accordance with many embodiments was tested on patients undergoing elective surgery to assess whether a CLV control could maintain MAP within ±5 mm Hg of a target MAP for at least 85% of an intraoperative period.

METHODS: Current practice is to maintain a MAP of at least 65 mm Hg, so the target MAP was set to 70 mm Hg as this results in the CLV controller aiming to keep the MAP between 65 and 75 mm Hg. This initially selected target could be modified during the case if needed. For patients having endovascular embolization of intracranial cerebral aneurysms, a target MAP of 80 mm Hg was used because the coils, flow diverters, and stents used to treat cerebral aneurysms reduce intracerebral blood flow and a higher MAP target is preferred in these cases. The CLV was switched on before induction of anesthesia (just after the placement of the radial arterial line). For safety reasons, norepinephrine was prepared and connected to an intravenous line using a separate infusion pump (but the administration rate was zero). In addition, no bolus of vasopressor (either ephedrine, phenylephrine, or even norepinephrine) was allowed during the procedures.

The predefined CLV goal was to maintain MAP within ±5 mm Hg of the target MAP using automated adjustments of the norepinephrine infusion rate. This target range (±5 mm Hg) was chosen for two reasons. First, it was felt to be a clinically reasonable definition for "tight" control around a chosen target. Second, in previous work it has been shown that clinicians do not maintain MAP within 10 mm Hg of preoperative values for at least 40% of the intraoperative duration. (See e.g., Rinehart, et al. Anaesth Crit Care Pain Med 2019; cited above.) Therefore, setting a high time-in-target at ±5 mm Hg would represent a significant improvement over current clinical practice.

The primary outcome measure was the percentage of time patients were hypotensive, as defined by a MAP of 5 mm Hg below the chosen target. (i.e., the time spent with a MAP <65 mm Hg for all cases except endovascular cerebral aneurysm cases, for which the value was <75 mm Hg).

Secondary outcomes include total dose of norepinephrine administered, percentage of treatment time spent in a hypertensive state, raw percentage "time in target," and standard performance criteria (colloquially known as Varvel's criteria). Percentage of treatment time in a hypertensive state was defined as MAP>5 mm Hg above the chosen target MAP with an active norepinephrine infusion (i.e., >75 or >85 mm Hg for endovascular cerebral aneurysm cases), while raw percentage of time in target was defined as the percentage of time spent during surgery with a MAP within ±5 mm Hg of the predefined MAP goal, and Varvel's criteria include were median absolute performance error (MDAPE), median prediction error (MDPE), wobble, and divergence (measured as mm Hg min$^{-1}$). (See e.g., Varvel J R, et al. Measuring the predictive performance of computer-controlled infusion pumps. J Pharmacokinet Biopharm 1992; 20: 63-94; the disclosure of which is herein incorporated by reference in its entirety.) The parameters within Varvel's criteria generally represent expected operating range of inaccuracy, bias, variability over time, and drift away from target over time, respectively. Additionally, a MAP above a set target can occur with no vasopressor infusion (e.g., CLV dose=0), so an ideal performance parameter was used that would not penalize calculated performance when a patient had an intrinsically higher blood pressure than the target with a CLV rate of 0—e.g., ideal performance=(time in target [%])+(time [%] above target MAP with CLV rate of 0). This calculation of an ideal performance parameter assists in calculating a parameter that controls for situations when time-over-target partially results from a poorly tuned controller that consistently overshoots the target then turns off.

Variables are presented as either a median value (25-75$^{th}$ percentile) or as a numerical amount with relevant percentage values. Hemodynamic variables (MAP, heart rate [HR], stroke volume [SV], CO, SVV) were recorded every 20 s by the EV1000 monitor (Edwards Lifesciences) and were subsequently averaged. Each patient's MAP status was classified as "in target" (MAP±5 mm Hg of the MAP target), "under target" (MAP>5 mm Hg below the MAP target), or "over target" (MAP>5 mm Hg above the MAP target with ongoing vasopressor infusion).

RESULTS: The predefined MAP target was set at 70 mm Hg in 16 subjects and at 80 mm Hg in the four patients who underwent endovascular embolization of intracranial cerebral aneurysm. Across all cases, the CLV controller was active for 3877 min (64.6 h) and was administering vasopressor for 97.1% of this time (3764 min, Table 5). The controller was active but not administering norepinephrine for 2.9% of case time because the patient's blood pressure was already at or above the target pressure. During the treatment time, the system made a total of 11,576 infusion rate changes (a median of three infusion rate changes per minute, a minimum of zero and maximum of four). Technical errors occurred in six of 20 subjects. The system stopped functioning twice in two subjects and once in four subjects. All errors were attributable to a pump communication error between the CLV system and the Q-core infusion pump related to third-party software in which the Commands Server software lost contact with the remote pump. An audible alarm sounded to alert the supervisor when this occurred and restarting the system immediately fixed the problem in every case. These processes lasted less than 2 min. The system was overridden once during a thoracic case when the MAP goal was deliberately decreased to 65 mm Hg for 30 min to help control bleeding. The system was never stopped for inappropriate drip rate management, and the additional line with the norepinephrine manually delivered by an infusion pump was never used.

Hypotension: Subjects were hypotensive (as defined by a MAP of 5 mm Hg below the chosen target) for 2.6% (1.6-4.6) of the total case time (range, 0-8.4%). Two subjects never had hypotension. The maximum hypotension time seen was 8.4% in a postoperative cardiac subject although this episode did not lead to any postoperative complications.

Norepinephrine Dose: The total dose of norepinephrine administered was 14,382 µg (i.e., 653 [499-810] µg per patient or a median dose of 3.9 µg min$^{-1}$ (Table 5). The maximum infusion rate reached was 15.74 µg min$^{-1}$ during a cerebral aneurysm procedure. FIG. 6 depicts the norepinephrine infusion rate (µg min$^{-1}$) over time for the 20 cases. FIG. 6 illustrates infusion rates over the first 2 h in all cases. The closed-loop vasopressor controller was started after placement of the arterial line and before anesthetic induction. In most patients the controller gives an initial large dose of vasopressor concurrent with induction as the blood pressure decreases because of the effects of the anesthetic drugs. After this, infusion rates diverge depending on the patient and case.

Percentage of Treatment Time in Hypertensive State: Subjects had a MAP over target for 2.4% (1.4-3.8) of case time when the CLV was still infusing norepinephrine. Patients had a MAP >10 mm Hg below target for 0.3% (0-0.6) of the time and a MAP >10 mm Hg above target (with active vasopressor infusion) for 0.2% (0-0.7) of the time. Thus, the system was more than 10 mm Hg away from the target around half-a-percent of case time in total.

Figure 8:
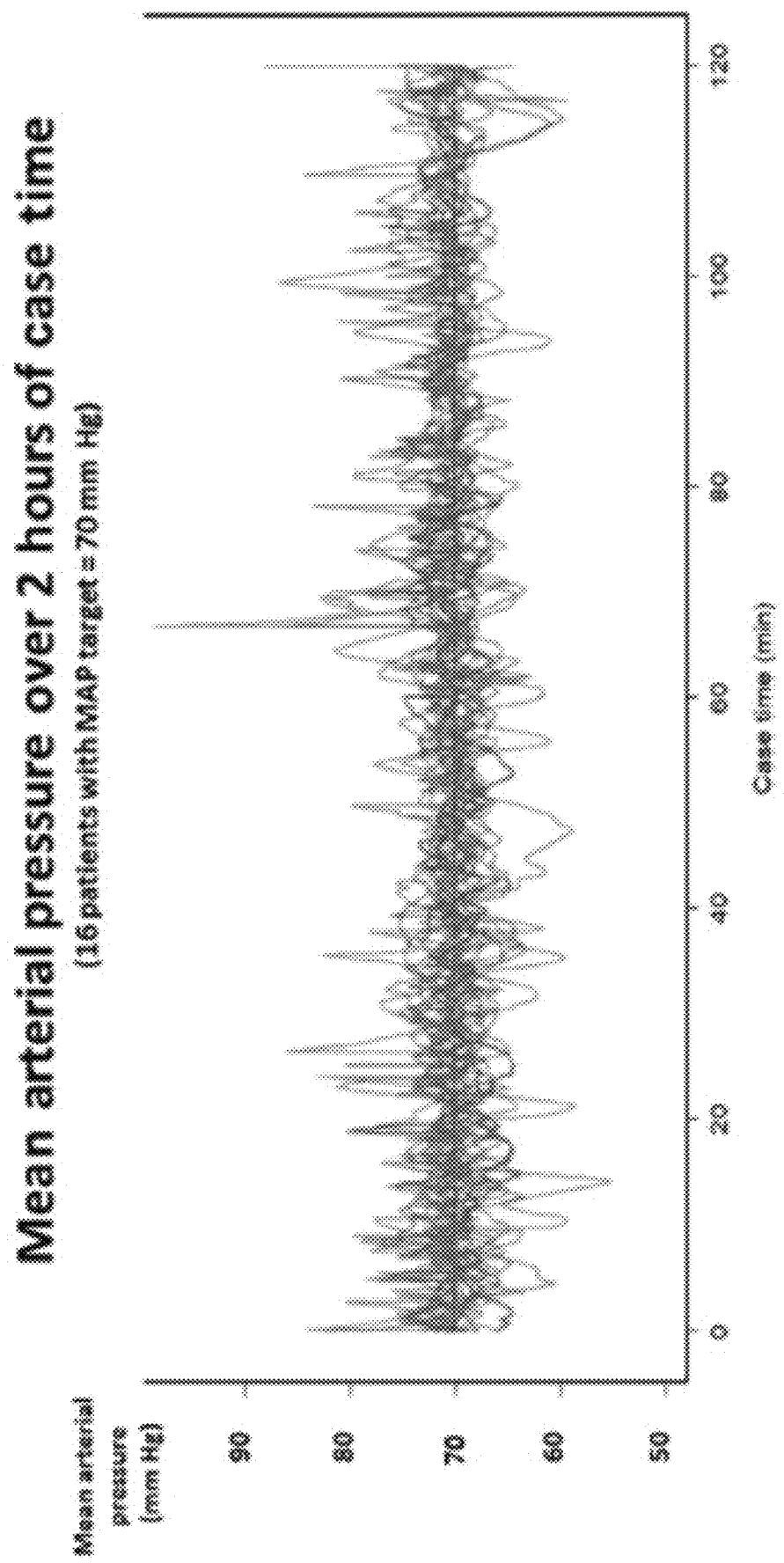
FIG. 8 illustrates mean arterial pressure (MAP) during procedures for multiple individuals being monitored with a closed loop system in accordance with embodiments of the invention.

Percentage of Time During Surgery with a MAP within ±5 mm Hg of MAP Goal: Subjects were in target (MAP±5 mm Hg of target) 91.6% (85.6-93.3) of the time. If allowing for correction of time-over-target when the vasopressor drip was zero, the "ideal performance" percentage of case time was 94.2% (91.8-95.8) (Table 5). There were two cases with 40 min of overall case time with MAP above target and the vasopressor rate was zero, eight such instances in four cases with times of 15-40 min, and the remaining 30 instances were 15 min or less in duration (FIG. 8). FIG. 8 illustrates MAP during the procedures for subjects with MAP targets of 70 mm Hg. Time-over-target when the vasopressor infusion was completely halted by the system is shown as zero error.

Performance Characteristics: The raw standard performance criteria for the controller without any correction were: MDAPE 2.9 (0.8); MDPE 0.5 (1.0); wobble 2.7 (0.8); and divergence (mm Hg min$^{-1}$) 0.0 (0.3). If allowing for correction of time over target when the vasopressor rate was zero ('ideal performance time'), the performance criteria were: MDAPE 2.1 (0.7); MDPE; 0.0 (0.7); wobble 2.3 (0.7); and divergence (mm Hg min$^{-1}$) 0.0 (0.3).

Clinical Outcomes: Except for the postoperative cardiac cases in the ICU which were kept intubated as part of their routine care, all subjects were extubated in the operating room at the end of the procedure. No subject was re-intubated. No patients experienced any major complications, but six subjects (30%) developed a minor postoperative complication (atrial fibrillation [n=1], pseudo-obstruction of the bowel [n=2], urinary tract infection [n=1], and other infections [n=2]). The PACU or ICU stay lasted 23 (20-24) h and the hospital stay 8 (5-12) days. No subject died during the 90-day follow-up period.

CONCLUSION: This proof-of-concept study demonstrates the clinical feasibility of a closed-loop system to reliably minimize perioperative hypotension using a norepinephrine infusion in patients undergoing moderate- and high-risk surgery in accordance with embodiments.

This proof-of-concept study found that titration of norepinephrine by the CLV controller in accordance with embodiments was able to maintain MAP within ±5 mm Hg of the predefined target for more than 90% of operative duration in subjects undergoing moderate- or high-risk surgery. The MAP was under target (hypotension) for 2.6% of the time (primary outcome) and above target (hypertension) with an infusion still running for 2.4% of the time. This contrasts with patients receiving manually adjusted vasopressor infusions, where a predetermined target MAP is achieved for <50% of operative time with >30% operative time exceeding the same MAP target.

While this system illustrates better control of an individual's blood pressure, it maintains a limitation in that aberrant and/or erroneous blood pressure readings could result in deviations from target due to a reliance on possibly invalid data. Thus, a closed-loop system illustrated within this example could benefit greatly from pre-validation systems and methods, such as those described within this disclosure.

Example 2: Detection of Arterial Blood Pressure Waveform Error Using Machine Learning Trained Algorithms BACKGROUND: In critically ill intensive care unit (ICU) patients and high-risk operating room (OR) patients, an invasive arterial pressure monitor is often placed so the blood pressure can be tracked beat-to-beat instead of intermittently. Many advanced hemodynamic monitors are now available which may derive or further extrapolate relevant patient parameters from the waveform such as measures of cardiac output, dynamic predictors of fluid responsiveness like pulse-pressure variation, and now even predictive measures are being derived which attempt to extrapolate future states of the patient (like pending hypotension) from the present signal. Moreover, there is active interest beyond analytics into closed-loop management whereby treatment may be guided automatically by analyses or measurements of the blood pressure waveform.

The arterial waveform pressure measurement, however, may be compromised by dampening, or the pressure transducer being at an inappropriate reference point. For example, during preparation of an OR patient for transport to the ICU, if the pressure transducer falls to the ground or off of the bed, the patient may appear to be acutely hypertensive and may be inappropriately treated based on this inaccurate reading. Human providers can visually check the level of the transducer to verify correct placement, and visually inspect the arterial pressure waveform for. Devices, particularly those downstream from the monitor itself, may not have these options, making mis-measurement a potential vulnerability and risk for mis-management, either by the device itself (for a closed-loop system) or by a provider making decisions based on information presented by the device (for an advanced or predictive hemodynamic monitor).

Methods

Patient Enrollment & Data collection: Patients aged 18 or older having surgery at UCI Medical Center and who were expected to have an invasive arterial blood pressure line placed as part of their anesthetic care were enrolled in the study. Patients who had non-sinus rhythm cardiac rhythms were excluded from the study. Following enrollment, induction and placement of all monitors and lines needed for the case was performed. No change in any aspect of the anesthesia care was made for this study and the anesthesia plan was left strictly to discretion.

Following induction and placement of lines once the patient was under maintenance and the primary anesthesia team settled, arterial blood pressure waveform was collected from the GE monitor. The waveform was captured using a National Instruments NI-9234 analog-to-digital converter connected to the defibrillation sync port on the GE Solar TRAM. The signal was recorded using custom software written by the authors in Microsoft Visual C# and sampled at a rate of 100 Hz. Data collection was allowed to continue for 15-30 minutes while ensuring the arterial blood pressure signal remained undampened and the transducer at an appropriate level for monitoring. This time was considered the "Normal" state and was deliberately longer than the other data collection periods in order to capture a sample of the normal case variation (i.e. changes in surgical stimulus, boluses of drugs like ephedrine and phenylephrine, changes in anesthetic depth, etc.).

After collection of the Normal data, three error states were sequentially introduced into the monitoring. First, the transducer was moved up above the patient sufficient to cause a 10-12 mmHg drop in MAP ("Transducer High" state). Second, the transducer was moved down below the patient sufficiently to cause a 10-12 mmHg rise in MAP above baseline ("Transducer Low"). Lastly, 0.5-0.75 cc of air were introduced into the arterial blood pressure fluid line sufficient to cause the minimum visually observable dampening in the waveform signal ("Dampened"). 3 minutes of data were collected in each of the error states, with an additional 3 minutes of Normal data collected between each error state. The additional normal data was collected between each error state to ensure any physiologic change in patient state (i.e. real blood pressure changes) during these periods was also sampled without the error to the extent possible, and to re-establish baseline between the different states.

The study state (Normal, Transducer High, Transducer Low, Dampened) was recorded alongside the recorded waveform data in the data file by the purpose-built capture software to ensure correct labeling of the waveform data in the dataset concurrent with its collection. The brief periods of time when adjustments were made to the transducer between states (to change from one to another) were additionally labeled as "Transition" periods so they could be excluded from analysis (since they will by definition contain a blend from one state to another). After introduction of the three error conditions, another 10 minutes of "Normal" data were collected to again ensure a large sample of normal case variation in the blood pressure signal.

Data Preparation and Featurization: After completion of data collection, each individual patient data file was run through a serial processing pathway and analyzed in ten-second segments referred to as "clips". All of the processing and machine learning software was written in Python 3.3.0. First, each ten-second clip was first run through a lowpass filter with a frequency cutoff of 0.025 and transition bandwidth of 0.3 before passing the waveform to beat-detection algorithm. Beat detection included a Fourier-transform for detection of the dominant time constants, selection of the most probable heart rate peak (those occurring in a range of 30-130 Hz, with higher weighted probability given to the middle of that range), then point-by-point scanning of the digitized waveform for peaks and troughs in the specified frequency. Following beat detection, anomalous beats and obvious non-physiologic data were removed by the algorithm. For example, arterial-line flushes resulting in values >250 mmHg were removed, as were beats that had high levels of noise (such as may occur when a patient is having motor-evoked potential monitoring).

Following the beat detection, each of the individual heart beats was assessed by a featurization algorithm. The features extracted included a total of 124 separate measurements of wave pressures (e.g. systolic, diastolic, mean, notch nadir or peak if a notch was present, pressures at time quantiles, etc.), times (e.g. beat time, systolic time, diastolic time, times between pressure quantiles, etc.), slopes (e.g. rise and fall slopes at different points in the pressure beat, slopes between peak and notch if present), ratio measures (e.g. peak pressure/notch pressure, systolic pressure/diastolic pressure, (systolic−diastolic)/mean, etc.), and specific morphology features (e.g. the presence of a notch in the wave, a double systolic peak, etc.). Each of the 124 measures was calculated for each beat found in the ten second clip and saved to a temporary working array. Finally, summary data for each clip was saved to a database (MariaDB 10.3, MariaDB Foundation, Delaware). For each ten-second clip, the median value for each extracted beat feature was recorded as a measure of location, and the ($75^{th}$ quantile value)−($25^{th}$ quantile value) was recorded as a measure of variance of the feature. This created a total feature set (including both median and interquartile range values of each feature and morphology features) of 252 measurements per wave clip. The transducer state was also recorded as well as the time stamp and sequence number of the clip in the overall waveform.

Data Calibration: Prior to machine learning & analysis, the data saved in the database was duplicated so that two different analysis methods could be performed. The first copy of the data was left as-is, with the raw feature measurements at each time point used in the machine learning (the "Uncalibrated" copy). The second copy of the data was transformed by calibrating the data to the initial measurements from each patient (the 'Calibrated' copy). Specifically, for each individual patient, the median value for each extracted waveform feature over the first three-minute time span of the first captured 'Normal' condition data was calculated and used as the baseline value for that feature and effectively became "zero". Each successive waveform clip was then re-calculated as raw difference from said baseline. For example, if the median pulse-pressure in the calibration frame period was 50 mmHg, and at some future state the pulse-pressure was 40 or 60, those values would be recalculated as change from baseline of −10 and +10 respectively in the calibrated copy. While the version of the final detection algorithms that might result from learning in this calibrated copy would add a requirement that the algorithm be clinically calibrated prior to use when in service, it was felt that this was worth the added potential value of allowing each individual patient's initial 'Normal' waveform to act as his or her own baseline, particularly if the sensitivity and specificity of the detection algorithm was significantly higher than for uncalibrated data. Moreover, calibration is a requirement in multiple modern hemodynamic monitoring systems and can typically be done in seconds, so the additional setup burden was not considered significant.

Machine Learning Protocol: After featurization of the patient waveforms, creation of machine-learning trained algorithms for prediction of transducer error conditions was begun. Machine learning was facilitated with the Python scikit-learn package.

First, the data was split into training and validation sets. It was decided that 75% of the collected data would be used as cross-training & test set, and 25% of data collected would be used as the validation set. Since multiple samples were collected for each patient, allowing samples from individual patients to be split into both the training and validation data sets could bias the results (allowing overfitting to occur via identification of unique patient characteristics in some conditions by some machine learning algorithms), so samples were separated on a per-patient basis, that is all samples from an individual patient went into either the training data or the validation set, never both, to ensure a complete and clean separation of patients in the two sets. Further, patient ID was not included in the data available to the machine learning algorithms.

Each of the three transducer error states (High, Low, Dampened) were independently trained and assessed for in separate iterations of the training processes versus the Normal condition (i.e. Normal vs. High, Normal vs. Low, Normal vs. Dampened) with the intent of creating a separate detection algorithm for each condition (as opposed to a single multi-class detection algorithm). While this would allow better focusing of the training on specific error states compared to a single multi-class detection algorithm, this would carry implications for the ultimate clinical application which are discussed below.

Once the training set was selected, feature expansion through transformation and combination were performed for each error state. First, each of the 'base' 252 features was assessed for prediction of the error state under consideration using a mutual information classifier. The highest mutual information score for any single base feature was identified and set as the 'cutoff' value for accepted transformed feature detection. Following this, each of the base features was sequentially tested as raw measurement or as transformed measurement (natural log, square, reciprocal) individually and then in combination with every other feature, itself both raw and transformed. Tested combinations included sums, differences, absolute differences and sums, ratios, and products. Any combined feature with a mutual information score higher than the cutoff was retained and added to the dataset.

Following feature expansion, a Monte-Carlo feature selection and machine-learning training pipeline was established. For feature selection, a "K-Best" selector was used with an f-classifier to select the features with the strongest relationships to the error state of interest. A count of features from 4-30 was tested. For this application, the Monte-Carlo pipeline included the following machine learning classifier algorithms: Linear Regressor, Ridge Regressor, Perceptron, Passive-Aggressive Regressor, Decision Trees, Support Vector Machines, K-Nearest Neighbors, Stochastic Gradient Descent, and Multilayer Perceptron neural net. Each iteration of the pipeline would select a random number of K-best features, one of the machine learning algorithms listed, and then choose from a randomized subset of available hyperparameters for the machine learning algorithm (if any). The balanced accuracy of each trained algorithm was checked in the training set using 10-fold cross-validation within the training set; balanced accuracy is simply accuracy (number of correct predictions divided by the total number of observations) balanced for the number of observations obtained on each individual class. For each iteration of the pipeline, the specific features selected, the algorithm, the hyperparameters, and the balanced accuracy were recorded.

A complete data preparation and training pipeline for this embodiment is illustrated in FIG. 8.

For each transducer error state, the above pipeline was allowed to run 10,000 samples to provide an arbitrarily large cross sample of performance. Following this, the pipeline was narrowed to the top 3 consistently performing algorithms and the range of the number of selected features reduced around the best performing sample sizes, and the pipeline re-run. From this latter pipeline the top performing algorithm and feature set was chosen as the final candidate algorithm for testing against the validation data set. Thus, in all, six final algorithms were produced by the pipeline—one for each error state (High, Low, Dampened) in both the calibrated and uncalibrated data sets.

Candidate Algorithm Evaluation: Each final candidate algorithm was at last tested against the 25% of the collected patients that were initially reserved with the goal of determining whether the algorithm might be clinically useful. 'Clinically useful' was a priori defined in this context as having sensitivity and specificity high enough that a receiver operating characteristic (ROC) curve generated from testing on the validation data had an area-under-the-curve (AUC) of 0.90 or greater. This would be sufficient, it was felt, to allow adjustment of the algorithm decision cutoff value to favor either precision or recall and minimize false alarms or missed alarms, depending on the clinical use of the algorithm. Each algorithm was scored based on the balanced accuracy in the training set, the ROC AUC of the algorithm performance in the validation set, and the precision-recall curve (PRC) AUC in the training set, since PRC AUC is thought to be more informative than ROC in unbalanced data sets 13. Precision is defined as true positives/(true positives+false positives), and recall is defined as true positives/(true positives+false negatives).

Statistics and Software: As noted, all coding and machine learning took place in Python 3.3.0. Statistical and performance analysis as well as plotting took place using Python or R (www.r-project.org). Variables are reported as count (%) for classes, and as mean±standard deviation for measures. Comparisons between groups were made by ANOVA (for scalar data) or chi-square test (for class data).

RESULTS: thirty-eight patients were recruited into the study from November 2019 to January 2020. The mean age was 52±15 years, 19 males and 19 females. Mean BMI was 27±4. Additional medical history and case types are shown in Table 6. All the arterial lines were placed in the radial artery by the primary teams: 24 (63%) in the left radial and 14 (37%) in the right.

From these patients a total of 40.1 hours of arterial line data was recorded which, when broken into ten-second analysis snips, resulted in 14,451 waveform snapshots. Of these snapshots, 2,569 were transitional states not used in the analysis and 1,149 were too noisy for the featurization algorithm to analyze (arterial line flushes or draws, patient positioning, or neuromonitoring motor-evoked potentials causing artifact, for example). This left 10,733 waveform snapshots included in the analysis. Of the analyzed 10-second snips, 1,100 (10%) were in the transducer 3 position, 1,065 (10%) were in the transducer 4 position, 765 (7.1%) were in the dampened position, and 7803 (72%) were collected with the transducer in the normal state (the imbalance being due to the long periods of normal data collection for adequate sampling of normal case variance). With a mean heart rate of 69±12 across the dataset (range 33-111), approximately 123,000 arterial line heartbeats in all were featurized during analysis.

Figure 9:
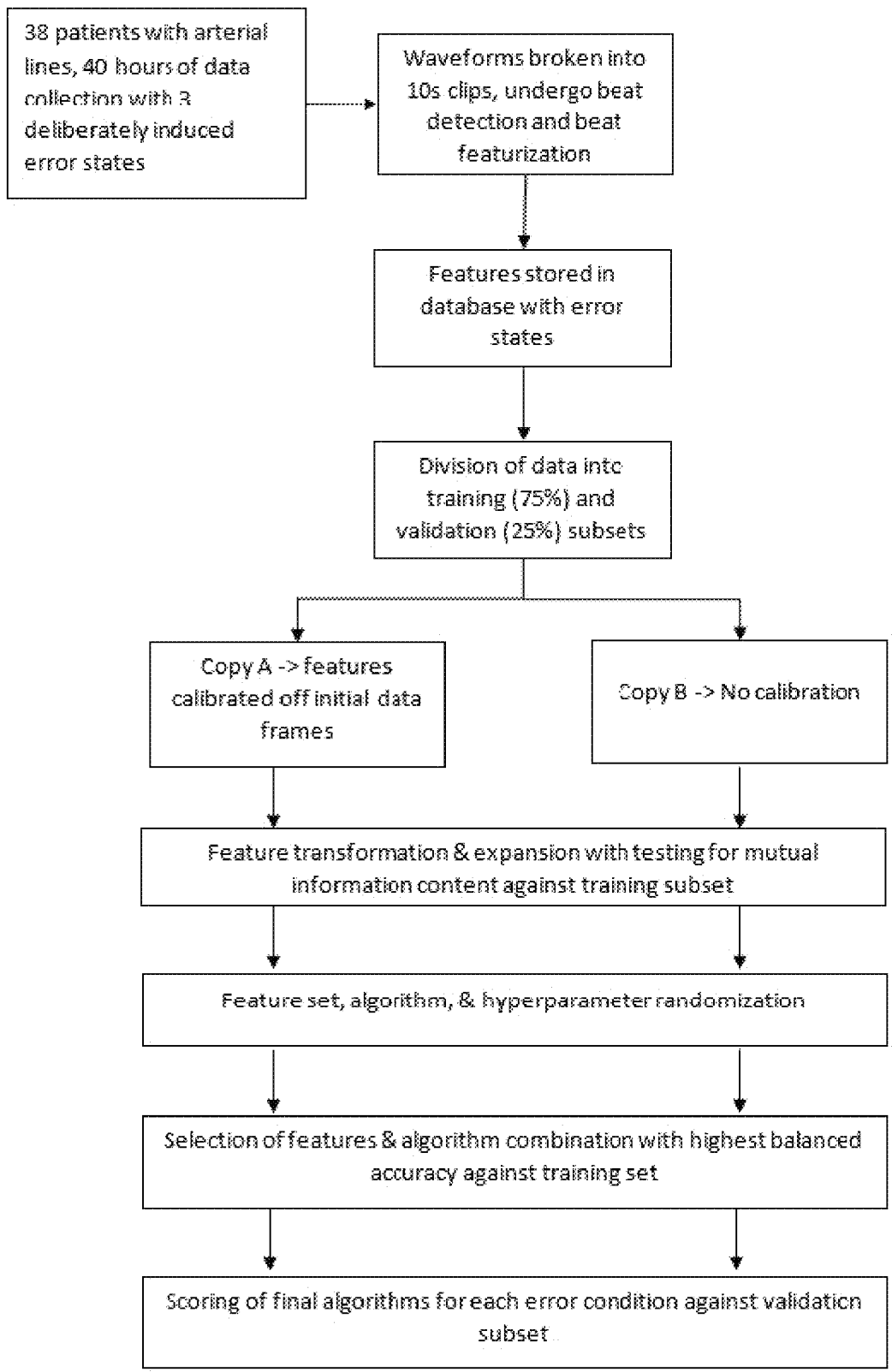
FIG. 9 illustrates flow chart of a method of selecting a machine learning algorithm in accordance with embodiments of the invention.
Figure 10:
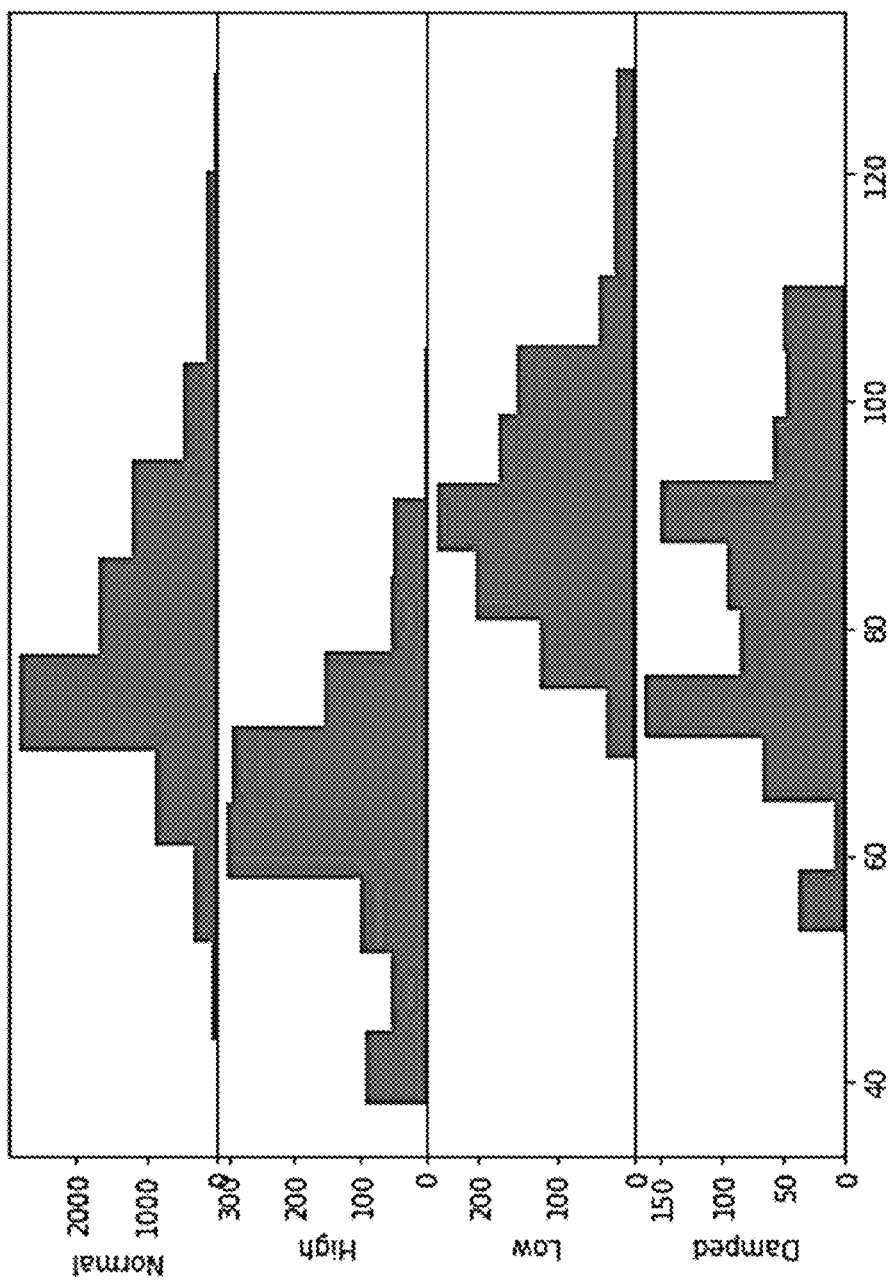
FIG. 10 illustrates histograms of MAP in various states in accordance with embodiments of the invention.

Heart rate was statistically significantly different across conditions ($p<0.0001$), presumably due random chance since it was not controlled in the study and collection times were arbitrary. The mean difference between the highest and lowest groups was only 3 beats per minute, however (Table 7), and the predictive accuracy of heart rate to Error State was negligible (ROC AUC=0.53, 0.52, 0.57 for transducer high, low, and dampened respectively). SBP and MAP varied as would be expected (rising when the transducer was low and falling when high). In the dampened condition, the MAP rose modestly compared to Normal (Table 7). Histograms of MAP in each condition are shown in FIG. 9. As hoped, by collecting long Normal data periods, there was significant overlap of the MAPs between the Normal condition and each of the other conditions, enough so that MAP alone was not an adequate predictor of Error State to meet acceptance criteria (ROC AUC=0.77, 0.75, and 0.59 for transducer high, low, and dampened respectively).

The best model for each of the three transducer error states (High, Low, Dampened) using either calibrated or uncalibrated data is shown in Table 4 along with the balanced accuracy score of the model in the training data set. Eight features were found to be optimal for two conditions, 12 features for three conditions, and 30 features selected for one condition (Uncalibrated/Transducer Low; Table 7). In all cases a Ridge Regression Classifier produced the best performing model with the exception of the Calibrated/Dampened condition where a simple linear regression classifier scored slightly higher (though it should be noted multiple models scored nearly perfectly in this condition). The performance of the trained models on the validation data set is also shown in Table 8. The ROC AUC ranged from 0.91-0.99 across all error states for both calibrated and uncalibrated data. The Dampened condition, using either calibrated and uncalibrated data had nearly perfect predictive capacity with AUC >0.99 in both cases. For each error state, the calibrated data set performed as well or better than the uncalibrated data. Similarly, precision/recall curve AUC's were greater than 0.9 for all conditions and whether calibrated or uncalibrated (again with calibrated data performing better), with the exception of the transducer low error state in the uncalibrated data method which had a PR AUC of 0.87. Finally, Youden's J statistic was calculated for each ROC curve to provide a single example point from which sensitivity and specificity could be demonstrated for each curve. The ROC curves themselves are shown in FIG. 4A and the PRC's shown in FIG. 4B.

CONCLUSION: This embodiment illustrates that machine-learning trained algorithms are capable of discriminating three transducer error conditions in our data set. The algorithms were trained and then validated on distinct subsets of the data without patient overlap between the sets. While the algorithms showed the best performance when the data was calibrated to the individual patient baseline, uncalibrated performance using raw data was also sufficient to achieve ROC AUC for sensitivity and specificity above 0.9 (the a priori goal) in all cases. In particular, the algorithm discriminated dampening of the arterial line extremely well, with AUC's >0.98 for the ROC and PR curves.

The condition most difficult to detect was the Transducer High condition using only raw data. This may not be surprising given that when the transducer is positioned to high relative to the patient, the blood pressure reading will be erroneously low, mimicking relative hypotension. Discriminating this erroneous hypotension from true hypotension in the data set appeared to be the most challenging for the machine learning algorithms over the available feature sets. It is possible that alternative featurizations of the waveform data may provide more suitable information. However, even given the relative challenge for this condition, sensitivity and specificity were still high enough across the range of the predictor variable that ROC AUC was greater than 0.9.

DOCTRINE OF EQUIVALENTS

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

TABLE 1

List of blood pressure waveform features, including category, an abbreviation, feature name and description, units and how features is measured and/or calculated.

| Feat No. | Feat Category | Feature Short Code | Feature Name | Feature Description | Measurement Units | Measurement/ Calculation |
|---|---|---|---|---|---|---|
| 1 | Rate | HR | Estimated HR | heart rate as estimated by low-resolution fast fourier transform | beats per min | measured |
| 2 | Rate | BHr | Measured beat heart rate | measured heart rate based on beat time | beats per min | measured (and = 60/ Bt) |
| 3 | Pressure (abs) | SBP | Systolic blood pressure | Maximum pressure during a beat | mmHg | measured |
| 4 | Pressure (abs) | DBP | Diastolic blood pressure ("minimum") | Lowest pressure during a beat | mmHg | measured |
| 5 | Pressure (abs) | FBP | Final blood pressure | Final pressure at the end of a beat (may not be lowest) | mmHg | measured |
| 6 | Pressure (abs) | MAP | Mean arterial pressure | The average of all pressures during a beat | mmHg | measured |
| 7 | Pressure (span) | PP | Pulse Pressure | The difference between the systolic and diastolic | mmHg | SBP-DBP |
| 8 | Pressure (abs) | DNn | Dicrotic notch nadir pressure | The pressure of the DN peak, if a notch is present. If none is present, the pressure at the maximum concavity of the beat downslope. | mmHg | measured |
| 9 | Pressure (abs) | DNp | Dicrotic notch peak pressure | The pressure of the DN nadir, if a notch is present. If none is present, the pressure at the maximum concavity of the beat downslope. | mmHg | measured |
| 10 | Pressure (span) | DNpp | Dicrotic notch pulse pressure | The difference between the dicrotic notch peak and nadir. May be 0. | mmHg | DNp − DNn |
| 11 | Pressure (abs) | TAIL10 | Tail Pressure at X | Pressure at point X % from the systolic peak to the end of the wave | mmHg | measured |
| 12 | Pressure (abs) | TAIL20 | Tail Pressure at X | Pressure at point X % from the systolic peak to the end of the wave | mmHg | measured |
| 13 | Pressure (abs) | TAIL30 | Tail Pressure at X | Pressure at point X % from the systolic peak to the end of the wave | mmHg | measured |
| 14 | Pressure (abs) | TAIL40 | Tail Pressure at X | Pressure at point X % from the systolic peak to the end of the wave | mmHg | measured |
| 15 | Pressure (abs) | TAIL50 | Tail Pressure at X | Pressure at point X % from the systolic peak to the end of the wave | mmHg | measured |
| 16 | Pressure (abs) | TAIL60 | Tail Pressure at X | Pressure at point X % from the systolic peak to the end of the wave | mmHg | measured |
| 17 | Pressure (abs) | TAIL70 | Tail Pressure at X | Pressure at point X % from the systolic peak to the end of the wave | mmHg | measured |
| 18 | Pressure (abs) | TAIL80 | Tail Pressure at X | Pressure at point X % from the systolic peak to the end of the wave | mmHg | measured |
| 19 | Pressure (abs) | TAIL90 | Tail Pressure at X | Pressure at point X % from the systolic peak to the end of the wave | mmHg | measured |
| 20 | Pressure | DNppq | Dicrotic Notch | DNpp as a fraction of the PP | none | DNpp/PP |

TABLE 1-continued

List of blood pressure waveform features, including category, an abbreviation, feature name and description, units and how features is measured and/or calculated.

| Feat No. | Feat Category | Feature Short Code | Feature Name | Feature Description | Measurement Units | Measurement/ Calculation |
|---|---|---|---|---|---|---|
| | Ratio | | pulse pressure quantile width | | | |
| 21 | Pressure (ref) | DNpq | Dicrotic notch peak quantile | DN peak pressure as a quantile of PP | none | (DNp − DBP)/PP |
| 22 | Pressure (ref) | DNnq | Dicrotic notch nadir quantile | DN nadir pressure as a quantile of PP | none | (DNn − DBP)/PP |
| 23 | Pressure Ratio | DNpr | Systolic/Dicrotic notch pressure ratio | Dicrotic notch pulse pressure to average pressure of DN | mmHg | DNpp/ ((DNp + DNn)/2) |
| 24 | Pressure Ratio | SDpr | Systolic to diastolic pressure ratio | The pulse pressure to average pressure ratio | none | PP/((SBP + DBP)/2) |
| 25 | Pressure Ratio | DnDpr | Dicrotic notch peak to diastolic blood pressure ratio | | none | DNp/DBP |
| 26 | Time | USt | Upswing time | Lag between lowest pre-beat pressure and systolic upswing | seconds | measured |
| 27 | Time | Bt | Beat time | Time between beat minima | seconds | measured |
| 28 | Time | St | Systole time | time from upswing to SBP | seconds | measured |
| 29 | Time | Dt | Diastole time; time from SBP peak to minimum | time from SBP to end of beat | seconds | measured |
| 30 | Time | pw95 | Pulse width X | Pulse width at X quantile in seconds | seconds | measured |
| 31 | Time | pw85 | Pulse width X | Pulse width at X quantile in seconds | seconds | measured |
| 32 | Time | pw75 | Pulse width X | Pulse width at X quantile in seconds | seconds | measured |
| 33 | Time | pw65 | Pulse width X | Pulse width at X quantile in seconds | seconds | measured |
| 34 | Time | pw55 | Pulse width X | Pulse width at X quantile in seconds | seconds | measured |
| 35 | Time | pw45 | Pulse width X | Pulse width at X quantile in seconds | seconds | measured |
| 36 | Time | pw35 | Pulse width X | Pulse width at X quantile in seconds | seconds | measured |
| 37 | Time | pw25 | Pulse width X | Pulse width at X quantile in seconds | seconds | measured |
| 38 | Tune | pw15 | Pulse width X | Pulse width at X quantile in seconds | seconds | measured |
| 39 | Time | DNnt_r | Dicrotic notch nadir lag time | time in seconds between the beginning of the beat and the DNn | seconds | nadir time − DN time |
| 40 | Time | DNpt_r | Dicrotic notch peak lag time | time in seconds between the beginning of the beat and the DNp | seconds | peak time − DN time |
| 41 | Time | DNnpt_r | Dicrotic notch nadir to peak time | time in seconds between DNn and DNp | seconds | DNpt − DNnt |
| 42 | Time Ratio | SDNt_r | time from systolic peak to dicrotic notch ratio | | none | measured |
| 43 | Time Ratio | SDtr | Systolic to diastolic time ratio | | none | (Dt − St)/((Dt + St)/2) |
| 44 | Time Ratio | Downt | downswing time | beat time at which tail begins to settle | none | measured |
| 45 | Time Ratio | Downt_r | downswing time ratio | beat time ratio at which tail begins to settle | none | measured |
| 46 | Time Ratio | pw95_r | Pulse width X | Pulse width at X quantile as ratio of beat time | none | pw(s)/Bt(s) |
| 47 | Time Ratio | pw85_r | Pulse width X | Pulse width at X quantile as ratio of beat time | none | pw(s)/Bt(s) |
| 48 | Time Ratio | pw75_r | Pulse width X | Pulse width at X quantile as ratio of beat time | none | pw(s)/Bt(s) |
| 49 | Time Ratio | pw65_r | Pulse width X | Pulse width at X quantile as ratio of beat time | none | pw(s)/Bt(s) |
| 50 | Time Ratio | pw55_r | Pulse width X | Pulse width at X quantile as ratio of beat time | none | pw(s)/Bt(s) |
| 51 | Time Ratio | pw45_r | Pulse width X | Pulse width at X quantile as ratio of beat time | none | pw(s)/Bt(s) |
| 52 | Time Ratio | pw35_r | Pulse width X | Pulse width at X quantile as ratio of beat time | none | pw(s)/Bt(s) |
| 53 | Time Ratio | pw25_r | Pulse width X | Pulse width at X quantile as ratio of beat time | none | pw(s)/Bt(s) |
| 54 | Time Ratio | pw15_r | Pulse width X | Pulse width at X quantile as | none | pw(s)/Bt(s) |

TABLE 1-continued

List of blood pressure waveform features, including category, an abbreviation, feature name and description, units and how features is measured and/or calculated.

| Feat No. | Feat Category | Feature Short Code | Feature Name | Feature Description | Measurement Units | Measurement/ Calculation |
|---|---|---|---|---|---|---|
| | | | | ratio of beat time | | |
| 55 | Time Ratio | PL95r | Pulse lag rise X | Lag from USt at rise time of XX quantile | none | measured, as ratio of Bt |
| 56 | Time Ratio | PL85r | Pulse lag rise X | Lag from USt at rise time of XX quantile | none | measured, as ratio of Bt |
| 57 | Time Ratio | PL75r | Pulse lag rise X | Lag from USt at rise time of XX quantile | none | measured, as ratio of Bt |
| 58 | Time Ratio | PL65r | Pulse lag rise X | Lag from USt at rise time of XX quantile | none | measured, as ratio of Bt |
| 59 | Time Ratio | PL55r | Pulse lag rise X | Lag from USt at rise time of XX quantile | none | measured, as ratio of Bt |
| 60 | Time Ratio | PL45r | Pulse lag rise X | Lag from USt at rise time of XX quantile | none | measured, as ratio of Bt |
| 61 | Time Ratio | PL35r | Pulse lag rise X | Lag from USt at rise time of XX quantile | none | measured, as ratio of Bt |
| 62 | Time Ratio | PL25r | Pulse lag rise X | Lag from USt at rise time of XX quantile | none | measured, as ratio of Bt |
| 63 | Time Ratio | PL15r | Pulse lag rise X | Lag from USt at rise time of XX quantile | none | measured, as ratio of Bt |
| 64 | Time Ratio | PL95f | Pulse lag fall X | Lag from USt at fall time of XX quantile | none | measured, as ratio of Bt |
| 65 | Time Ratio | PL85f | Pulse lag fall X | Lag from USt at fall time of XX quantile | none | measured, as ratio of Bt |
| 66 | Time Ratio | PL75f | Pulse lag fall X | Lag from USt at fall time of XX quantile | none | measured, as ratio of Bt |
| 67 | Time Ratio | PL65f | Pulse lag fall X | Lag from USt at fall time of XX quantile | none | measured, as ratio of Bt |
| 68 | Time Ratio | PL55f | Pulse lag fall X | Lag from USt at fall time of XX quantile | none | measured, as ratio of Bt |
| 69 | Time Ratio | PL45f | Pulse lag fall X | Lag from USt at fall time of XX quantile | none | measured, as ratio of Bt |
| 70 | Time Ratio | PL35f | Pulse lag fall X | Lag from USt at fall time of XX quantile | none | measured, as ratio of Bt |
| 71 | Time Ratio | PL25f | Pulse lag fall X | Lag from USt at fall time of XX quantile | none | measured, as ratio of Bt |
| 72 | Time Ratio | PL15f | Pulse lag fall X | Lag from USt at fall time of XX quantile | none | measured, as ratio of Bt |
| 73 | Time | DNnt | Dicrotic notch nadir time | Lag from USt at dicrotic notch nadir | seconds | measured |
| 74 | Time | DNpt | Dicrotic notch peak time | Lag from USt at dicrotic notch peak | seconds | measured |
| 75 | Time | DNnpt | Dicrotic notch nadir to peak time | time from dicrotic nadir to dicrotic peak | seconds | measured |
| 76 | Time | SDNt | Systolic to dicrotic notch time | time from systolic peak to dicrotic notch | seconds | measured |
| 77 | Time Ratio | IQ95ppr | Interquartile X pre-post systolic ratio | Quantile QQ pre-SBP to post-SBP ratio | none | (SysTime − PLQQr)/ (PLQQf − SysTime) |
| 78 | Time Ratio | IQ85ppr | Interquartile X pre-post systolic ratio | Quantile QQ pre-SBP to post-SBP ratio | none | (SysTime − PLQQr)/ (PLQQf − SysTime) |
| 79 | Time Ratio | IQ75ppr | Interquartile X pre-post systolic ratio | Quantile QQ pre-SBP to post-SBP ratio | none | (SysTime − PLQQr)/ (PLQQf − SysTime) |
| 80 | Time Ratio | IQ65ppr | Interquartile X pre-post systolic ratio | Quantile QQ pre-SBP to post-SBP ratio | none | (SysTime − PLQQr)/ (PLQQf − SysTime) |
| 81 | Time Ratio | IQ55ppr | Interquartile X pre-post systolic ratio | Quantile QQ pre-SBP to post-SBP ratio | none | (SysTime − PLQQr)/ (PLQQf − SysTime) |
| 82 | Time Ratio | IQ45ppr | Interquartile X pre-post systolic ratio | Quantile QQ pre-SBP to post-SBP ratio | none | (SysTime − PLQQr)/ (PLQQf − SysTime) |
| 83 | Time Ratio | IQ35ppr | Interquartile X pre-post systolic ratio | Quantile QQ pre-SBP to post-SBP ratio | none | (SysTime − PLQQr)/ (PLQQf − SysTime) |
| 84 | Time Ratio | IQ25ppr | Interquartile X pre-post systolic ratio | Quantile QQ pre-SBP to post-SBP ratio | none | (SysTime − PLQQr)/ (PLQQf − SysTime) |
| 85 | Time Ratio | IQ15ppr | Interquartile X pre-post systolic ratio | Quantile QQ pre-SBP to post-SBP ratio | none | (SysTime − PLQQr)/ (PLQQf − SysTime) |
| 86 | Time Ratio | PL95r_r | Pulse lag ratio at Xth percentile on rise slope | time delay from beat start to identified feature | none | Time/Bt |
| 87 | Time Ratio | PL85r_r | Pulse lag ratio at Xth percentile on rise slope | time delay from beat start to identified feature | none | Time/Bt |
| 88 | Time Ratio | PL75r_r | Pulse lag ratio at Xth percentile on rise slope | time delay from beat start to identified feature | none | Time/Bt |
| 89 | Time Ratio | PL65r_r | Pulse lag ratio at | time delay from beat start to | none | Time/Bt |

TABLE 1-continued

List of blood pressure waveform features, including category, an abbreviation, feature name and description, units and how features is measured and/or calculated.

| Feat No. | Feat Category | Feature Short Code | Feature Name | Feature Description | Measurement Units | Measurement/ Calculation |
|---|---|---|---|---|---|---|
| 90 | Time Ratio | PL55r_r | Pulse lag ratio at Xth percentile on rise slope | time delay from beat start to identified feature | none | Time/Bt |
| 91 | Time Ratio | PL45r_r | Pulse lag ratio at Xth percentile on rise slope | time delay from beat start to identified feature | none | Time/Bt |
| 92 | Time Ratio | PL35r_r | Pulse lag ratio at Xth percentile on rise slope | time delay from beat start to identified feature | none | Time/Bt |
| 93 | Time Ratio | PL25r_r | Pulse lag ratio at Xth percentile on rise slope | time delay from beat start to identified feature | none | Time/Bt |
| 94 | Time Ratio | PL15r_r | Pulse lag ratio at Xth percentile on rise slope | time delay from beat start to identified feature | none | Time/Bt |
| 95 | Time Ratio | PL95f_r | Pulse lag ratio at Xth percentile on fall slope | time delay from beat start to identified feature | none | Time/Bt |
| 96 | Time Ratio | PL85f_r | Pulse lag ratio at Xth percentile on fall slope | time delay from beat start to identified feature | none | Time/Bt |
| 97 | Time Ratio | PL75f_r | Pulse lag ratio at Xth percentile on fall slope | time delay from beat start to identified feature | none | Time/Bt |
| 98 | Time Ratio | PL65f_r | Pulse lag ratio at Xth percentile on fall slope | time delay from beat start to identified feature | none | Time/Bt |
| 99 | Time Ratio | PL55f_r | Pulse lag ratio at Xth percentile on fall slope | time delay from beat start to identified feature | none | Time/Bt |
| 100 | Time Ratio | PL45f_r | Pulse lag ratio at Xth percentile on fall slope | time delay from beat start to identified feature | none | Time/Bt |
| 101 | Time Ratio | PL35f_r | Pulse lag ratio at Xth percentile on fall slope | time delay from beat start to identified feature | none | Time/Bt |
| 102 | Time Ratio | PL25f_r | Pulse lag ratio at Xth percentile on fall slope | time delay from beat start to identified feature | none | Time/Bt |
| 103 | Time Ratio | PL15f_r | Pulse lag ratio at Xth percentile on fall slope | time delay from beat start to identified feature | none | Time/Bt |
| 104 | Area | AUC | Area under the curve | Area under the pressure wave treating DBP as zero | mmHg * s | $\Sigma(mmHg)$ |
| 105 | Area | AUB | Area under the beat | Area under beat, equal to DBP * Bt | mmHg * s | $\Sigma(mmHg)$ |
| 106 | Area | AUC25 | Area under the curve for PW25 region | AUC for beat that exceeds 25th quantile of pressure | mmHg * s | $\Sigma(mmHg)$ |
| 107 | Area | AUC50 | Area under the curve for PW50 region | AUC for beat that exceeds 50th quantile of pressure | mmHg * s | $\Sigma(mmHg)$ |
| 108 | Area | AUC75 | Area under the curve for PW75 region | AUC for beat that exceeds 75th quantile of pressure | mmHg * s | $\Sigma(mmHg)$ |
| 109 | Area | AUCpr | AUC pre-peak (DBP to SBP) | AUC for beat prior to SBP | mmHg * s | $\Sigma(mmHg)$ |
| 110 | Area | AUCpo | AUC post-peak (SBP to DBP) | AUC for beat following SBP | mmHg * s | $\Sigma(mmHg)$ |
| 111 | Area | AUCs | AUC systole (upswing to dicrotic notch | AUC for beat from start to DN | mmHg * s | $\Sigma(mmHg)$ |
| 112 | Area | AUCd | AUC diastole (dicrotic notch to end of wave) | AUC for beat from DN to end of wave | mmHg * s | $\Sigma(mmHg)$ |
| 113 | Slope | R1a | Segment slope (angle) USP --> IQ25 | Segment slope | mmHg/sec | $(p2 - p1)/(t2 - t1)$ |
| 114 | Slope | R2a | Segment slope (angle) 25 --> 50 | Segment slope | mmHg/sec | $(p2 - p1)/(t2 - t1)$ |
| 115 | Slope | R3a | Segment slope | Segment slope | mmHg/sec | $(p2 - p1)/(t2 - t1)$ |

TABLE 1-continued

List of blood pressure waveform features, including category, an abbreviation, feature name and description, units and how features is measured and/or calculated.

| Feat No. | Feat Category | Feature Short Code | Feature Name | Feature Description | Measurement Units | Measurement/ Calculation |
|---|---|---|---|---|---|---|
| 116 | Slope | R4a | Segment slope (angle) 50 --> 75 | Segment slope | mmHg/sec | (p2 − p1)/(t2 − t1) |
| 117 | Slope | R5a | Segment slope (angle) 75 --> 95 | Segment slope | mmHg/sec | (p2 − p1)/(t2 − t1) |
| 118 | Slope | F1a | Segment slope (angle) 95 --> SBP | Segment slope | mmHg/sec | (p2 − p1)/(t2 − t1) |
| 119 | Slope | F2a | Segment slope (angle) SBP --> 95f | Segment slope | mmHg/sec | (p2 − p1)/(t2 − t1) |
| 120 | Slope | F3a | Segment slope (angle) 95f --> 75f | Segment slope | mmHg/sec | (p2 − p1)/(t2 − t1) |
| 121 | Slope | F4a | Segment slope (angle) 75f --> 50f | Segment slope | mmHg/sec | (p2 − p1)/(t2 − t1) |
| 122 | Slope | F5a | Segment slope (angle) 50f --> 25f | Segment slope | mmHg/sec | (p2 − p1)/(t2 − t1) |
| 123 | Slope | Sa | Segment slope (angle) 25f --> FBP | Segment slope | mmHg/sec | (p2 − p1)/(t2 − t1) |
| 123 | Slope | Sa | Systolic slope (USp --> SBP) | Slope from feature to feature | mmHg/sec | (p2 − p1)/(t2 − t1) |
| 124 | Slope | Da | Diastolic slope (SBP --> FBP) | Slope from feature to feature | mmHg/sec | (p2 − p1)/(t2 − t1) |
| 125 | Slope | SDNa | SBP --> DNp | Slope from feature to feature | mmHg/sec | (p2 − p1)/(t2 − t1) |
| 126 | Slope | DNnpa | DNn --> DNp | Slope from feature to feature | mmHg/sec | (p2 − p1)/(t2 − t1) |
| 127 | Slope | DNEa | DNp --> FBP | Slope from feature to feature | mmHg/sec | (p2 − p1)/(t2 − t1) |
| 128 | Morphology | WW | Weird Wave | binary indicator of a third peak in the median waveform | none | measured |
| 129 | Morphology | WW_Pre | Weird wave pre-SBP | binary indicator that the WW occurs pre-peak | none | measured |
| 130 | Morphology | WW_Post | Weird wave post-SBP | binary indicator that the WW occurs post-peak/pre DN | none | measured |
| 131 | Morphology | WW_PostDN | Weird wave post dicrotic notch | binary indicator that the WW occurs post-DN | none | measured |
| 132 | Morphology | WW_Press | Weird wave peak's pressure value | measured pressure at the WW peak | mmHg | measured |
| 133 | Morphology | WW_DoubleSys | Weird wave double-systolic | binary indicator that the systolic peak is notched (different from the dicrotic notch) | none | measured |
| 134 | Morphology | WW_SysDist | Weird wave systolic distance | measured time lag between WW and systolic peak | none | measured |

TABLE 2

Features used in exemplary models; X indicates feature used in particular model, including models to detect arterial line transducer is too high (2 versions), to detect arterial line transducer is too low (2 versions), and to detect dampening. Feature abbreviations are explained in Table 1.

| Feature | Arterial Trans. too High v. 1 | Arterial Trans. too Low v. 1 | Dampening | Arterial Trans. too High v. 2 | Arterial Trans. too Low v. 2 |
|---|---|---|---|---|---|
| Intercept | X | X | X | X | X |
| AUC | X | X | | | |
| AUB | X | X | | X | X |
| AUCpo | X | X | | | |
| AUCs | X | X | | | |
| AUCd | X | X | | | |
| DBP | X | X | | X | X |
| FBP | X | X | | X | X |
| MAP | X | X | | | |
| DNn | X | X | | | |
| DNp | X | X | | | |
| SDpr | | X | X | X | X |
| DnDpr | | X | | | |
| PP | | | X | | |
| TAIL10 | | | X | | |
| TAIL40 | | | X | | |
| TAIL50 | | | X | | |
| TAIL60 | | | X | | |
| R1a | | | X | | |
| R2a | | | X | | |
| MAPz | | | | | X |
| Hz_AUC | | | | X | |
| Hz_AUB | | | | X | X |
| Hz_AUCpo | | | | X | X |
| Hz_DBP | | | | X | X |
| Hz_FBP | | | | X | X |
| Hz_SDpr | | | | X | X |

TABLE 3

Decision Matrix for fluid and vasopressor preference systems

| VP State | Prefer Vasopressor | Neutral | Prefer Fluid |
|---|---|---|---|
| Current Vasopressor Rate Increasing | Normal Closed Loop Fluid Controller ("CLF") | Prompt new test bolus for significant increase in vasopressor rate (e.g. 25% increase) | Prompt new test bolus for significant increase in vasopressor rate (e.g. 15% increase) Decrease in Vasopressor dose, or increase in MAP, following Fluid bolus counts as positive bolus* |
| Current Vasopressor Rate is Stable Above Zero | CLF does not give test boluses | Normal CLF | Decrease in Vasopressor dose, or increase in MAP, following Fluid bolus counts as positive bolus* |
| Current Vasopressor Rate is Zero | CLF does not give test boluses | Normal CLF | Decrease in Vasopressor dose, or increase in MAP, following Fluid bolus counts as positive bolus* |
| Current Vasopressor Rate isDecreasing | CLF does not give test boluses | Normal CLF | Decrease in Vasopressor dose, or increase in MAP, following Fluid bolus counts as positive bolus* |

TABLE 4

Fluid Delivery Multiplier in Alternate Closed Loop Fluid Controller Model

| | Mean Arterial Pressure | | | | | | | | |
|---|---|---|---|---|---|---|---|---|---|
| SVV | <50 | 50-54 | 55-59 | 60-64 | 65-69 | 70-74 | 75-79 | 80-84 | 85+ |
| <8 | 4 | 3 | 2 | 1 | 0 | 0 | 0 | 0 | 0 |
| 8-10 | 4 | 4 | 3 | 2 | 1 | 1 | 0 | 0 | 0 |
| 10-12 | 6 | 6 | 6 | 3 | 2 | 1 | 0 | 0 | 0 |
| 12-14 | 8 | 8 | 6 | 4 | 3 | 2 | 1 | 0 | 0 |
| 14-16 | 10 | 10 | 8 | 5 | 4 | 3 | 2 | 1 | 0 |
| >16 | 10 | 10 | 8 | 6 | 5 | 4 | 2 | 1 | 0 |

TABLE 5

Performance of a CLV system.

| | | Mean percentage of case time with | | | | | Total number of | | Mean |
|---|---|---|---|---|---|---|---|---|---|
| Case type | Ideal performance (%)* | MAP ± 5 mm Hg of target | MAP > 5 mm Hg below target | MAP > 5 mm Hg above target | MAP > 5 Hg above target with VP | CLV giving VP | CLV rate changes per case | CLV rate changes per hour | rate of VP (μg min$^{-2}$) |
| Thoracic | 96.9 | 87.6 | 1.5 | 10.9 | 1.6 | 89.6 | 445 | 200 | 4.01 |
| Thoracic | 91.9 | 78.9 | 3.2 | 17.9 | 4.9 | 84.5 | 297 | 175 | 1.89 |
| Thoracic | 89.5 | 76.5 | 2.8 | 20.7 | 7.7 | 74.5 | 437 | 163 | 1.37 |
| Thoracic | 94.1 | 92.6 | 3.9 | 3.5 | 2 | 98.5 | 724 | 215 | 3.52 |
| Vascular | 99.2 | 99 | 0 | 1 | 0.8 | 99.3 | 478 | 176 | 4.03 |
| Vascular | 95.8 | 82.3 | 1.2 | 16.5 | 3 | 86.1 | 480 | 183 | 1.28 |
| Vascular | 85.8 | 83 | 5.2 | 11.8 | 9 | 96.5 | 1624 | 238 | 4.2 |
| Vascular | 88.3 | 66.2 | 3.7 | 30.1 | 8 | 75.4 | 1119 | 155 | 3.5 |
| Whipple | 99 | 93 | 0 | 7 | 1 | 91.8 | 900 | 134 | 2.61 |
| Whipple | 94.1 | 94.1 | 5.9 | 0 | 0 | 98.3 | 275 | 159 | 4.27 |
| Whipple | 95.1 | 90.9 | 2.5 | 6.6 | 2.4 | 94.5 | 697 | 200 | 2.71 |
| Whipple | 92.6 | 86.4 | 2.5 | 11.2 | 4.9 | 89.1 | 1032 | 221 | 2.42 |
| Neuro aneurysm | 95.9 | 95.8 | 1.5 | 2.6 | 2.6 | 100 | 415 | 174 | 2.56 |
| Neuro aneurysm | 95.7 | 91.6 | 2.3 | 6.1 | 2 | 95.8 | 440 | 143 | 3.74 |
| Neuro aneurysm | 95.9 | 95.9 | 1.7 | 2.4 | 2.4 | 100 | 503 | 206 | 9.69 |
| Neuro aneurysm | 94.3 | 92.6 | 2.2 | 5.2 | 3.5 | 97.7 | 453 | 170 | 4.9 |
| ICU postop cardiac | 94.9 | 94.9 | 4.6 | 0.5 | 0.5 | 100 | 250 | 108 | 4.06 |
| ICU postop cardiac | 90.2 | 90.2 | 6.7 | 3.1 | 3.1 | 100 | 386 | 245 | 6.93 |
| ICU postop cardiac | 91.6 | 91.6 | 8.4 | 0 | 0 | 99.5 | 322 | 153 | 4.12 |
| ICU postop cardiac | 93.2 | 91.8 | 4.8 | 3.4 | 2 | 98.5 | 299 | 152 | 7.65 |
| Median | 94.2 | 91.6 | 2.6 | 5.6 | 2.4 | 97.1 | 449 | 172 | 3.9 |
| 25th percentile | 91.8 | 85.6 | 1.6 | 2.5 | 1.4 | 89.5 | 370 | 154.5 | 2.6 |

TABLE 5-continued

Performance of a CLV system.

| Case type | Ideal performance (%)* | Mean percentage of case time with | | | | CLV giving VP | Total number of | | Mean rate of VP (µg min$^{-2}$) |
|---|---|---|---|---|---|---|---|---|---|
| | | MAP ± 5 mm Hg of target | MAP > 5 mm Hg below target | MAP > 5 mm Hg above target | MAP > 5 Hg above target with VP | | CLV rate changes per case | CLV rate changes per hour | |
| 75th percentile | 95.8 | 93.3 | 4.6 | 11.3 | 3.8 | 99.3 | 703.8 | 201.2 | 4.2 |

*Ideal performance time % = (MAP ± 5 mm Hg) + time above target when CLV is zero.

TABLE 6

Patient Demographics and Case Data.

| Demographics | (n = 38) |
|---|---|
| Age | 52 ± 15 |
| BMI | 27 ± 4 |
| Gender | |
| Male | 19 (50%) |
| Female | 19 (50%) |
| Arterial Line Location | |
| Right | 14 (37%) |
| Left | 24 (63%) |
| Procedure Type | |

TABLE 7

Heart Rate and Blood Pressures in Collected Data.

| State | Samples | HR | SBP | MAP |
|---|---|---|---|---|
| Normal | 10,733 | 70+/−13 | 111+/−17 | 80+/−12 |
| Transducer High | 1,100 | 69+/−11 | 97+/−15 | 64+/−11 |
| Transducer Low | 1,065 | 69+/−11 | 125+/−18 | 93+/−12 |
| Dampened | 765 | 67+/−8 | 98+/−14 | 83+/−13 |

TABLE 8

Trained Algorithms and Validation Test Results.

| | Training | | | Validation | | | | |
|---|---|---|---|---|---|---|---|---|
| Condition | Method | Number of Features in Final Model | ML Model | Balanced Accuracy | ROC AUC | PRC AUC | Y-Index Sensitivity* | Y-Index Specificity* |
| Transducer High | Calibrated | 8 | Ridge Regression Classifier | 0.93 | 0.95 | 0.95 | 0.98 | 0.92 |
| Transducer Low | Calibrated | 12 | Ridge Regression Classifier | 0.90 | 0.94 | 0.93 | 0.92 | 0.83 |
| Dampened | Calibrated | 12 | Linear Regression Classifier | 0.99 | >0.99 | >0.99 | 0.99 | 0.99 |
| Transducer High | Uncalibrated | 12 | Ridge Regression Classifier | 0.91 | 0.91 | 0.87 | 0.94 | 0.74 |
| Transducer Low | Uncalibrated | 30 | Ridge Regression Classifier | 0.92 | 0.93 | 0.91 | 0.92 | 0.80 |
| Dampened | Uncalibrated | 8 | Ridge Regression Classifier | 0.99 | >0.99 | 0.98 | 0.98 | 0.92 |

*Youden's J-index: The location on the ROC curve that maximizes Youden's J-statistic, which itself is defined as (sensitivity + specificity − 1). ML: machine learning; ROC: receiver operator characteristic; AUC: area under the curve; PR: precision recall curve TABLE 6-continued Patient Demographics and Case Data.

| Demographics | (n = 38) |
|---|---|
| Hepatobiliary | 8 (21%) |
| Neuro | 13 (34%) |
| Abdominal | 2 (5%) |
| Vascular | 3 (8%) |
| Spine | 5 (13%) |
| Other | 7 (18%) |
| Relevant History | |
| CAD | 3 (8%) |
| Vascular Disease | 4 (10%) |
| Smoking History | 7 (23%) |
| Diabetes | 4 (10%) |
| Fontan Physiology | 1 (3%) |
| Renal Failure | 2 (5%) |

What is claimed is:

1. A method for validating waveform reliability and controlling fluid infusion comprising
continuously capturing, using one or more transducers, a blood pressure measurement from a patient and generating a blood pressure waveform;
validating, using a waveform reliability evaluator, a reliability of the continuous waveform, wherein the waveform reliability evaluator comprises a machine learning algorithm, wherein validating a reliability of the continuous waveform comprises:
receiving physiological measurements as a continuous blood pressure waveform derived from the one or more transducers,
identifying features from the continuous blood pressure waveform, and
computing, using the identified features as input into the machine learning algorithm, a waveform reliability output; and
pumping fluid into the patient via a fluid pump, wherein a control module receives physiological measurement data from the continuously captured physiological measurements and the computed waveform reliability output to control infusion rate of the fluid pump based on the physiological measurement data and the waveform reliability output.

2. The method of claim 1, wherein the validating step further comprises:
detecting, using the waveform reliability evaluator, individual beat within the blood pressure waveform; and
assessing, using the waveform reliability evaluator, each individual beat with a featurization algorithm to extract the features.

3. The method of claim 2, wherein the features comprise one or more of: measurements of wave pressure, times of a beat, slopes of a beat, ratio measures of wave pressures, and morphological features of the waveform.

4. The method of claim 1, wherein the waveform reliability output comprises an assessment of transducer position or dampening of waveform signal.

5. The method of claim 1, wherein the waveform reliability output is a quantitative measure of 0-100% confidence.

6. The method of claim 1, wherein the waveform reliability output is a semi-quantitative measure of not reliable, possibly reliable, certainly reliable.

7. The method of claim 1, wherein the transducer captures the blood pressure waveform invasively or non-invasively.

8. The method of claim 1, wherein the blood pressure waveform is inferred from an additional physiological measurement.

9. The method of claim 8, wherein the other physiological measurement is selected from electrocardiography, photoplethysmography, skin stretch sensor, or electrical impedance or induction.

10. The method of claim 1 further comprising:
obtaining an additional physiological measurement as a second continuous waveform;
validating a reliability of the second continuous waveform; and
outputting a second reliability measure of the second validated waveform reliability.

11. The method of claim 10, wherein the additional physiological measurement is selected from the group consisting of electrocardiography photoplethysmography, skin stretch sensor, or electrical impedance or induction.

12. The method of claim 1, wherein the one or more transducers is in connection with a clinical monitor.

13. A system for evaluating waveform reliability and controlling fluid infusion comprising:
one or more transducers for continuously capturing physiological measurements from a patient and generating a blood pressure waveform;
a waveform reliability evaluator comprising a machine learning algorithm for determining waveform reliability;
a control module; and
a fluid pump for infusing fluid into the patient;
wherein the waveform reliability evaluator is configured to:
receive physiological measurements as a continuous blood pressure waveform derived from the one or more transducers,
identify features from the continuous blood pressure waveform, and compute, using the identified features as input into the machine learning algorithm, a waveform reliability output;
wherein the control module is configured to:
receive physiological measurement data from the continuously captured physiological measurements and the computed waveform reliability output, and
control infusion rate of the fluid pump based on the physiological measurement data and the waveform reliability output.

14. The device of claim 13, wherein the fluid pump infuses a cardioactive drug.

15. The device of claim 14, wherein the cardioactive drug is selected from the group consisting of a blood pressure regulator, a cardiac rate regulator, a cardiac contractility regulator, and a vasomotor tone regulator.

16. The device of claim 13 wherein the cardioactive drug is a vasopressor.

17. The device of claim 13, wherein the fluid pump infuses a fluid, wherein the fluid is selected from the group consisting of: a crystalloid, a colloid, and a blood product.

18. The device of claim 13, wherein the one or more transducers is in connection with a clinical monitor.

19. The device of claim 13 further comprising a second fluid pump;
wherein the fluid pump infuses a fluid selected from the group consisting of:
a crystalloid, a colloid, and a blood product; and
wherein the second fluid pump infuses a cardioactive drug.

20. The device of claim 19, wherein the cardioactive drug is selected from the group consisting of a blood pressure regulator, a cardiac rate regulator, a cardiac contractility regulator, and a vasomotor tone regulator.

21. The device of claim 19 wherein the cardioactive drug is a vasopressor.

22. The device of claim 13, wherein the waveform reliability evaluator is further configured to identify features from the continuous blood pressure waveform by:
detecting individual beats within the blood pressure waveform; and
assessing each individual beat with a featurization algorithm to extract the features.

23. The device of claim 22, wherein the features comprise one or more of: measurements of wave pressures, times of a beat, slopes of a beat, ratio measures of wave pressures, and morphological features of the waveform.

24. The device of claim 13, wherein the waveform reliability output comprises an assessment of transducer position or dampening of waveform signal.

* * * * *